United States Patent
Runyon et al.

(10) Patent No.: US 10,087,211 B2
(45) Date of Patent: Oct. 2, 2018

(54) ANDROSTANE AND PREGNANE STEROIDS WITH POTENT ALLOSTERIC GABA RECEPTOR CHLORIDE IONOPHORE MODULATING PROPERTIES

(71) Applicants: RESEARCH TRIANGLE INSTITUTE, Research Triangle Park, NC (US); The United States of America, as represented by the Secretary, Department of Health and Human Services, Bethesda, MD (US)

(72) Inventors: Scott P. Runyon, Hillsborough, NC (US); Michael Rogawski, Sacramento, CA (US); Edgar Cook, Fairfax Station, VA (US); John Kepler, Raleigh, NC (US); Hernan Navarro, Chapel Hill, NC (US); Rafal Kaminski, Waterloo (BE); Matthew Orr, Raleigh, NC (US)

(73) Assignees: RESEARCH TRIANGLE INSTITUTE, Research Triangle Park, NC (US); THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 15/341,573

(22) Filed: Nov. 2, 2016

(65) Prior Publication Data

US 2017/0051008 A1 Feb. 23, 2017

Related U.S. Application Data

(60) Continuation of application No. 13/974,633, filed on Aug. 23, 2013, now Pat. No. 9,518,080, which is a
(Continued)

(51) Int. Cl.
| | |
|---|---|
| *C07J 7/00* | (2006.01) |
| *C07J 41/00* | (2006.01) |
| *C07J 31/00* | (2006.01) |

(52) U.S. Cl.
CPC ............. *C07J 41/0005* (2013.01); *C07J 7/00* (2013.01); *C07J 31/003* (2013.01)

(58) Field of Classification Search
CPC ......... C07J 41/0005; C07J 7/00; C07J 31/003
(Continued)

(56) References Cited

U.S. PATENT DOCUMENTS

| | | |
|---|---|---|
| 2,753,361 A | 7/1956 | Dodson et al. |
| 2,763,669 A | 9/1956 | Dodson et al. |

(Continued)

FOREIGN PATENT DOCUMENTS

| | | |
|---|---|---|
| EP | 0 291 717 A1 | 11/1988 |
| JP | 9-510701 | 10/1997 |

(Continued)

OTHER PUBLICATIONS

Supplementary Search Report dated Apr. 28, 2011 in European Patent Application No. 08771137.0-1211/2155204.
(Continued)

*Primary Examiner* — Barbara P Badio
(74) *Attorney, Agent, or Firm* — Oblon, McClelland, Maier & Neustadt, L.L.P.

(57) ABSTRACT

This invention describes compounds of Structures 1, 2, and 3 and their use as allosteric modulators of the GABA receptor chloride ionophore complex to alleviate stress, anxiety, mood disorders, seizures, depression, treatment of drug and alcohol abuse, memory, premenstrual disorders, and neural system damage.

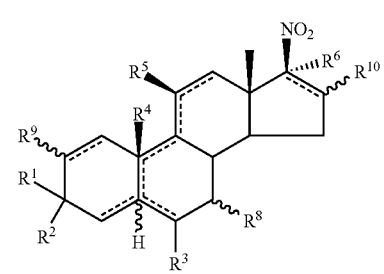

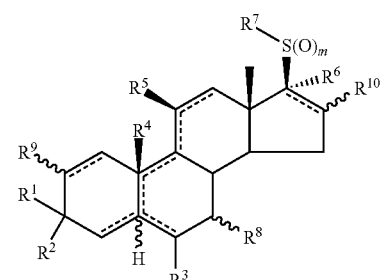

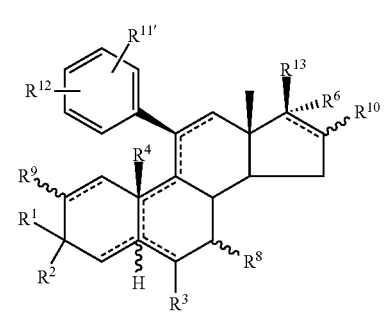

3 Claims, 5 Drawing Sheets

Related U.S. Application Data division of application No. 12/664,470, filed as application No. PCT/US2008/067059 on Jun. 16, 2008, now Pat. No. 8,575,375.

(60) Provisional application No. 60/944,257, filed on Jun. 15, 2007.

(58) Field of Classification Search
USPC .................. 552/522, 525, 599; 514/182
See application file for complete search history.

(56) References Cited

U.S. PATENT DOCUMENTS

| | | | |
|---|---|---|---|
| 2,847,427 | A | 8/1958 | Sollman et al. |
| 3,001,986 | A | 9/1961 | Burtner et al. |
| 3,094,521 | A | 6/1963 | Patchett et al. |
| 3,094,522 | A | 6/1963 | Patchett et al. |
| 4,891,367 | A | 1/1990 | Angelastro et al. |
| 6,143,736 | A | 11/2000 | Upasani et al. |

FOREIGN PATENT DOCUMENTS

| | | |
|---|---|---|
| JP | 5663303 B2 | 12/2014 |
| WO | WO 93/03732 A1 | 3/1993 |
| WO | WO 95/21617 | 8/1995 |

OTHER PUBLICATIONS

John. F. W. Keana, et al., "Synthesis and Characterization of a Novel Cholesterol Nitroxide Spin Label. Application to the Molecular Organization of Human High Density Lipoprotein", Journal of the American Chemical Society, XP002275442, vol. 103, No. 16, Jan. 1, 1981, pp. 4904-4912.

Michael Jarman, et al., "The 16,17-Double Bond is Needed for Irreversible Inhibition of Human Cytochrome P450$_{17\alpha}$by Abiraterone (17-(3-Pyridyl)androsta-5, 16-dien-3β-ol) and Related Steroidal Inhibitors", Journal of Medicinal Chemistry, XP002633115, vol. 41, 1998, pp. 5375-5381.

Swann D.A. et al., "Axial and Equatorial Thiols-III 17א and 17β-Mercapto Derivatives of Androstane and Androstan-3βOL", Tetrahedron, vol. 24, No. 3, pp. 1441 to 1411, (1968).

Patchett, A.A. et al., "The Synthesis of 17β-Amino-17א )lyhteyxobrac-'2(-androstane Lactams1", J. Org. Chem., vol. 27, pp. 3822 to 3828, Nov. 1962.

Supplementary Search Report dated May 17, 2011, in European Patent Application No. 08771137.0.

Communication Pursuant to Article 94(3) EPC dated Feb. 15, 2012, in European Patent Application No. 08 771 137.0.

Rosanna Tedesco, et al., "Novel Stereoselective Synthesis of 11β-Carbon-Substituted Estradiol Derivatives", J. Org. Chem., vol. 60, No. 16, XP55018883, 1995, pp. 5316-5318.

Canadian Office Action dated Jul. 18, 2012 in Patent Application No. 2,698,172.

Canadian Office Action dated Feb. 12, 2013 in Patent Application No. 2,698,172.

L.N.Nysted, et al., "Steroidal Aldosterone Antaganists. VI", Journal of Organic Chemistry, 1962, vol. 27, pp. 3175-3177.

Office Action dated Mar. 19, 2013, in Japanese Patent Application No. 2010-512418, filed Jun. 16, 2008 (w/English-language translation).

Patent Examination Report dated May 2, 2013, in Australian Patent Application No. 2008265898, filed Jun. 16, 2008.

Office Action dated Jun. 2, 2014, in Japanese Patent Application No. 2010-512418 with English translation.

Office Action dated Aug. 17, 2015 in Japanese Patent Application No. 2014-202979 (with English language translation).

$ED_{50} = 5.3\ (4.6\text{-}6.1)$ mg/kg
$ED_{50} = 8.8\ (7.1\text{-}10.8)$ mg/kg
$ED_{50} = 13.7\ (12.0\text{-}15.5)$ mg/kg All drugs injected i.p., 15 min. before seizure testing a) NBS, dioxane, KHCO$_3$, NaBH$_4$ a) 1) Benzylthiol, TsOH, AcOH, 2) KOH, MeOH
b) Na, NH$_3$, THF, Et$_2$O
c) Lithium tri-t-butoxyaluminum hydride
d) MeI, NaHCO$_3$
e) MCPBA, 0° CH$_2$Cl$_2$
f) MCPBA, CH$_2$Cl$_2$ a) Li, NH₃, t-butanol, THF
b) Trimethylsulfoxonium iodide, NaH, DMSO
c) LiAlH₄, THF
d) Tetrapropylammonium perruthenate, 4-methylmorpholine-N-oxide, CH₂Cl₂
e) NH₂OH HCl, pyridine
f) MCPBA, CH₂Cl₂
g) NBS, dioxane, KHCO₃, NaBH₄,
h) FeSO₄, H₂O

ANDROSTANE AND PREGNANE STEROIDS WITH POTENT ALLOSTERIC GABA RECEPTOR CHLORIDE IONOPHORE MODULATING PROPERTIES

CROSS REFERENCE TO RELATED APPLICATIONS

The present application is a continuation of U.S. Ser. No. 13/974,633, filed Aug. 23, 2013, now allowed, which is a divisional of U.S. Ser. No. 12/664,470, filed May 5, 2010, now U.S. Pat. No. 8,575,375, which is a 371 application of PCT/US08/67059, filed Jun. 16, 2008, and claims priority to U.S. Provisional Ser. No. 60/944,257, filed Jun. 15, 2007.

BACKGROUND OF THE INVENTION

Field of Invention

The present invention relates to androstane and pregnane steroid compounds and their use as allosteric modulators of the GABA receptor chloride ionophore complex and their use to alleviate stress, anxiety, mood disorders, seizures, depression, treatment of drug and alcohol abuse, memory, premenstrual disorders, and neural system damage.

Discussion of the Background

The present invention encompasses methods and compounds related to endogenous metabolites of androstane and pregnane steroids. Certain endogenous steroids including allopregnanolone (3α-hydroxy-5α-pregnane-20-one) and the A-ring reduced metabolite of progesterone are potent stereoselective positive allosteric modulators of GABA receptors (Belelli and Lambert, 2005). These neurosteroids, like other agents that potentiate the activity of GABA receptors, exhibit anxiolytic, sedative-hypnotic, anticonvulsant, and general anesthetic actions. Allopregnanolone and A-ring reduced neurosteroids generally lack classical hormonal activity mediated by nuclear hormone receptors. Given their GABA receptor modulating activity, natural neurosteroids could potentially be used therapeutically (Gasior et al., 1999). However, they do not have ideal properties as drug substances. Natural neurosteroids can be metabolically converted to hormonally active substances (Rupprecht, 2003) and have poor bioavailability. Consequently, there is an unmet need for synthetic analogs with improved pharmacokinetic and pharmacodynamic properties. Structural modifications at the 3-position inhibit metabolism of the secondary 3-hydroxyl substituent, but permit GABA receptor modulating activity to be retained (Hogenkamp et al., 1997). One such analog, ganaxalone, the 3β-methyl derivative of allopregnanolone, is currently in clinical development for epilepsy (Monaghan et al., 1999; Rogawski, 2006).

Substitution of the allopregnanolone 17-position with a variety of functional groups allows GABA receptor modulating activity to be retained. For example, the naturally occurring neurosteroids, allotetrahydrodeoxycorticosterone (5α,3α-THDOC), androstenediol, and androsterone, which have O=CCH$_2$OH, alcohol, and keto substituents at the 17-position have GABA receptor modulating activity as does the prototype allopregnanolone, which has an acetyl substituent at the 17-position. In addition, the synthetic 17β-carbonitrile analog exhibits GABA receptor modulatory potency and efficacy similar to allopregnanolone (Wittmer et al., 1996).

Interestingly, the natural (16-17 unsaturated) pheromone, 3α-androstenol, lacks a 17-position substituent yet retains GABA receptor modulating activity, albeit of reduced potency (Kaminski et al., 2006). Taken collectively, these data indicate a critical role for GABA modulators based on the neuroactive steroid scaffold for treatment of a variety of disease states.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1A and 1B are graphical representations of the results obtained when A-2a was evaluated in the elevated zero maze test of anxiolytic activity. The percentage of time spent in open arms of the maze (FIG. 1A) as well as the number of entries (FIG. 1B) were significantly enhanced with therapeutic doses of A-2a.

SUMMARY OF THE INVENTION

Figure 1A:
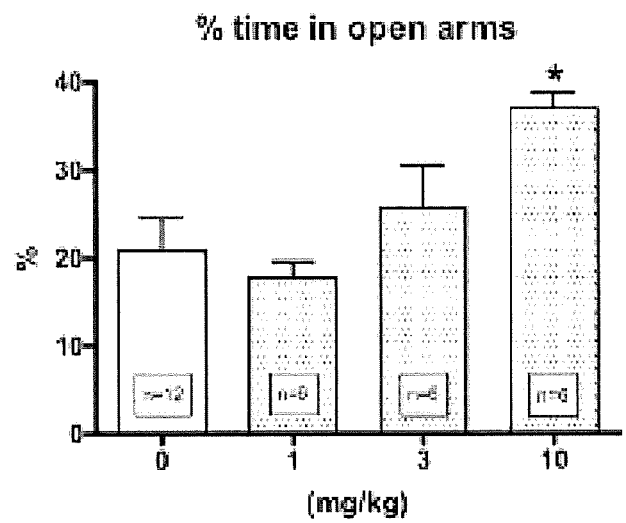
Figure 1B:
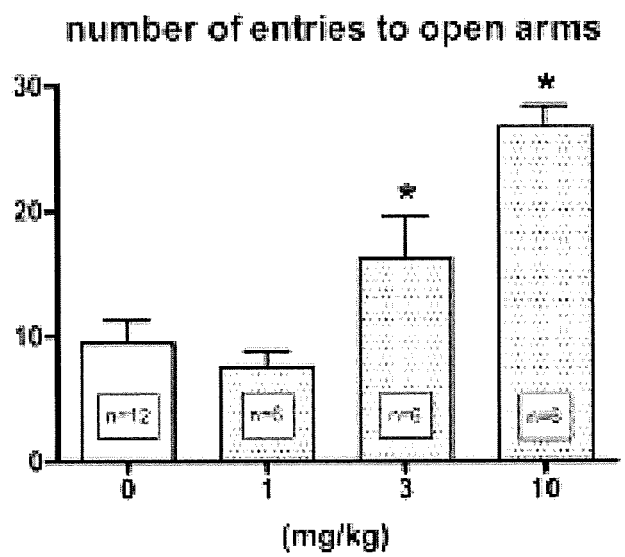
Figure 2:
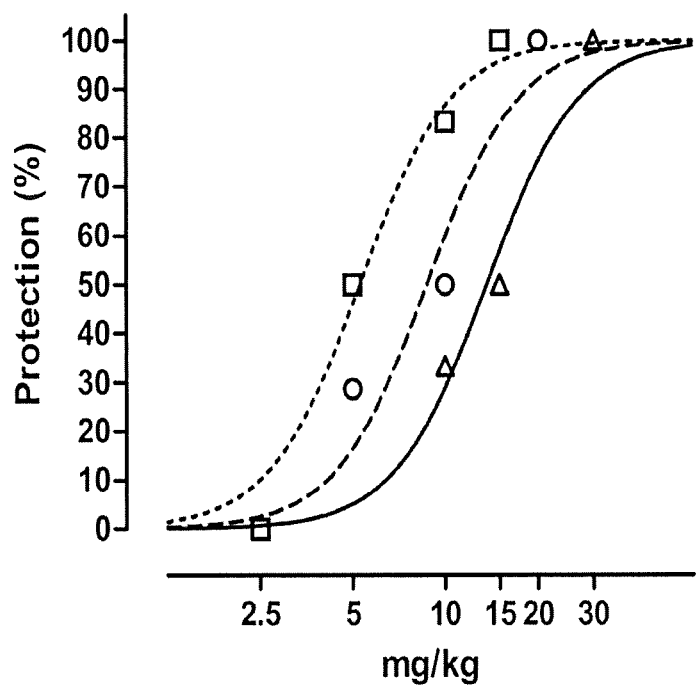
FIG. 2 is a graphical representation showing the percent protection provided by A-2a, A-2b, and B-5 from pentylenetetrazole (PTZ) induced seizures. Compounds exhibited potent anticonvulsant activity in the EC$_{50}$ range of 5-13 nM.
Figure 3:
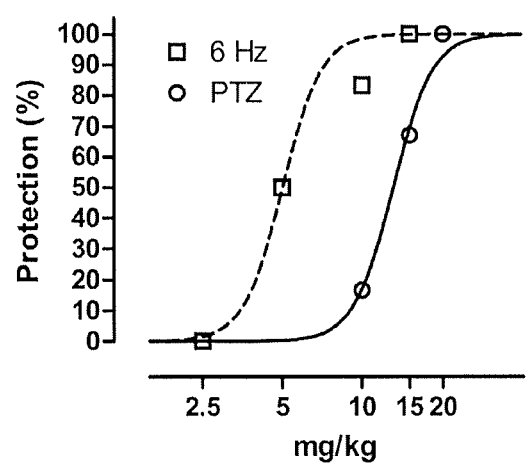
FIG. 3 is a graphical representation of the examination of A-2a, in two different seizure models demonstrating the ability of this synthetic neuroactive steroid to reduce both chemically (PTZ) and electrically (6 Hz) induced seizures in mice.

Accordingly, one object of the present invention is to provide novel pregnane and androstane steroids having allosteric GABA activity.

A further object of the present invention is to provide methods for using these novel compounds in the treatment of convulsions, epilepsy, depression, drug and alcohol abuse, anxiety, memory problems, and neural system damage in humans or animals.

These and other objects of the present invention, either alone or in combinations thereof, have been satisfied by the discovery of steroid derivatives having formula 1, 2, or 3 below:

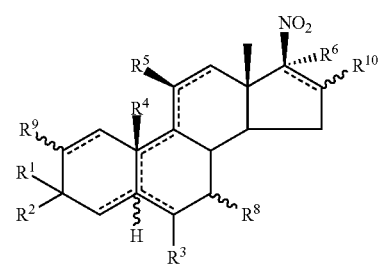

1

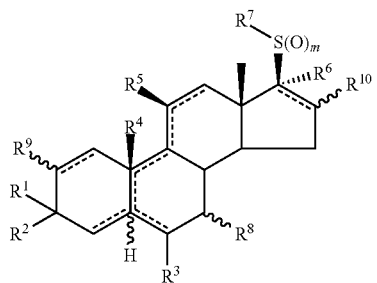

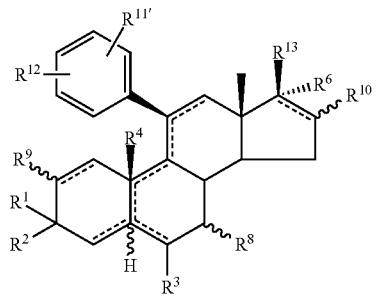

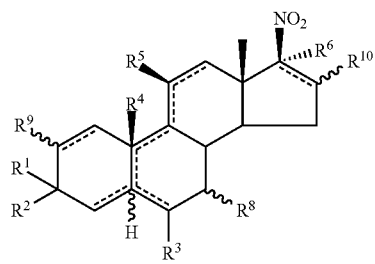

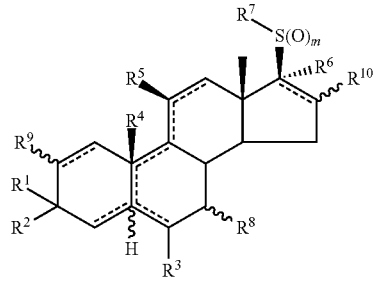

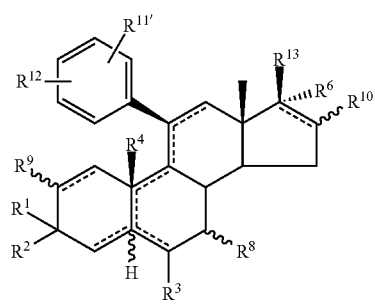

DETAILED DESCRIPTION OF THE INVENTION

The present invention expands upon the structural features on pregnane and androstane steroids previously been found to be associated with allosteric GABA activity. It thus provides an array of compounds from which may be obtained additional analogs with improved pharmacological and pharmacokinetic properties. Prior art describes the utility of the 17β-acetyl substituent in steroidal 3α-ols for GABA activity. In this work we show that a 17β-nitro group or 17-thioalkyl group serve as a bioisostere for 17β-acetyl and when combined with the 3α-OH-5α-H of androstane and pregnane steroid systems full agonist activity and equipotency with allopregnanolone in the [$^3$H]-flunitrazepam assay is observed for GABA activity. These derivatives are also equipotent with allopregnanolone in the [$^{35}$S]TBPS assay for GABA.

The effect on GABA allosteric potency via substitution at the 11β-position with aromatic groups has not been previously examined for androstane and pregnane steroids having a 3α-OH, 5α-H. In this work we now demonstrate that substitution at the 11β-position with an alternately substituted aromatic group provides androstane and pregnane steroids with enhanced GABA allosteric potency compared to allopregnanolone in both the [$^{35}$S]FBPS assay for GABA and the [$^3$H]-flunitrazepam assay. Novel structural features disclosed in this application include the 17β-nitro group, 17β-thiomethyl group, and the 11β-(4-dimethylaminophenyl) group. These functional groups will possess different solubility, metabolism and pharmacokinetic properties from the 17β-acetyl and 11β-H compounds of previous inventions. These may aid in formulation or dosing. In addition, some of the compounds are excellent intermediates for further modifications. Such compounds may be of use in epilepsy, depression, anxiety, treatment of drug and alcohol abuse, memory, premenstrual disorders, neural system damage and other potentially therapeutic areas.

The steroid derivatives of this invention are those comprised of the above mentioned structural formulas 1, 2, or 3.

Within the scope of the present invention, the term heteroatom means oxygen, nitrogen, sulfur, silicon or boron. Halogen means fluorine, chlorine, bromine or iodine and halo means fluoro, chloro, bromo or iodo. Aralkyl, aralkenyl, or aralkynyl means a $C_1$-$C_4$ alkyl, $C_2$-$C_4$ alkenyl or $C_2$-$C_4$ alkynyl group bearing an aryl substituent. Lower alkyl means a $C_1$-$C_6$ alkyl group. Heteroaryl means a unit of 5 to 12 non-hydrogen atoms consisting of one or more cyclic structures that may be fused or linked together, which contain 1 to 5 heteroatoms and which are generally accepted by those skilled in the art as having aromatic electronic character.

Heteroaralkyl, heteroaralkenyl, or heteroaralkynyl means a $C_1$-$C_4$ alkyl, $C_2$-$C_4$ alkenyl, or $C_2$-$C_4$ alkynyl group bearing a heteroaryl substituent.

"Optionally substituted" means unsubstituted or substituted with one or more heteroatom(s) and/or halogens and/or alkyl groups of 1 to 4 carbon atoms and/or alkenyl and/or alkynyl groups of 2 to 4 carbon atoms and/or cycloalkyl groups of 3 to 7 carbon atoms and/or aryl groups of 6 to 12 carbon atoms and/or heteroaryl groups, and in which the alkyl, alkenyl, alkynyl, cycloalkyl, aryl or heteroaryl group may be further substituted with one or more heteroatoms and/or halogens. Substitution may occur directly on $CH_2$ groups of cyclic amine heterocycles. Where their valency permits, heteroatoms may be substituted either within the carbon chain or by attachment to it by single or double bonds. For example, —$CH_2CH_2C(=O)H$, —$CH_2(C=O)CH_3$, —$CH_2CH_2OCH_3$, —$CH_2CH_2CH_2OH$, $CH_3CH_2CH_2O-$, $CH_2CH_2C(=O)NH_2$, $CH_3CH_2C(=O)NH-$, $CH_2CH_2COOCH_3$, $CH_3CH_2COO-$, and $CF_3CC-$ all fall within this definition.

In all cases where valency and steric considerations permit, alkyl, alkenyl, alkynyl and cycloalkyl groups may contain additional double or triple bonds and/or branched chains.

In one embodiment of the invention, the group $R^1$ as it appears in structure 1 may be H or (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle; 2-heterocycle-substituted ethynyl, heterocycle-substituted $C_{1-4}$ alkyl, heterocycle-substituted $C_{2-4}$-alkenyl, or heterocycle-substituted $C_{3-6}$ cycloalkyl;

the $R^2$ group is OH or $OR^{14}$, where $R^{14}$ is HCO— or (optionally substituted) $C_{1-18}$ alkyl-CO— (except that $R^{14}$ is not $CH_3$ when $R^1$, $R^2$, $R^3$, $R^5$, $R^6$, $R^8$, $R^9$ and $R^{10}$=H, $R^4$=$CH_3$, and there are no double bonds present), $C_{2-18}$ alkenyl-CO—, $C_{2-18}$ alkynyl-CO—, $C_{6-10}$ aryl-CO— or heterocycle-CO—; or $R^{14}$ is (optionally substituted) $C_{1-18}$ alkyl-X—CO—, $C_{2-18}$ alkenyl-X—CO—, $C_{2-18}$ alkynyl-X—CO—, $C_{6-10}$ aryl-X—CO— or heterocycle-X—CO—, where X is O or $NR^{11}$, where $R^{11}$ is (optionally substituted) $C_{1-4}$ alkyl, $C_{3-6}$ cycloalkyl, $C_{2-4}$ alkenyl, $C_{2-4}$ alkynyl $C_{6-10}$ aryl or heterocycle; or $R^{14}$ is trimethylsilyl or triethylsilyl; or $R^{14}$ is (optionally substituted) $C_{1-4}$ alkyl, $C_{3-6}$ cycloalkyl, $C_{2-4}$ alkenyl, or $C_{2-4}$ alkynyl, or; or $R^{14}$ is HO—$SO_2$— or a salt thereof or $R^2$ is $NR^{15}R^{16}$, where $R^{15}$ is H, OH or (optionally substituted) $C_{1-4}$ alkyl, $C_{3-6}$ cycloalkyl, $C_{2-4}$ alkynyl, $C_{2-4}$ alkenyl, $C_{6-10}$ aryl, heterocycle or $R^{15}$ is $OR^{17}$, where $R^{17}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, $C_{1-18}$ alkyl-CO—, $C_{2-18}$ alkenyl-CO—, $C_{2-18}$ alkynyl-CO—, $C_{6-10}$ aryl-CO— or heterocycle-CO—; and where $R^{16}$ is H or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, or $R^{16}$ is H—CO— or (optionally substituted) $C_{1-18}$ alkyl-CO—, $C_{2-18}$ alkenyl-CO—, $C_{2-18}$ alkynyl-CO—, $C_{3-6}$ cycloalkyl-CO—, $C_{6-10}$ aryl-CO— or heterocycle-CO—;

$R^3$ is H, halogen, cyano, azido or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle;

$R^4$ is H or (optionally substituted) Me;

$R^5$ is H, halogen, azido, cyano, thiocyano, =O, OH, $OR^{16}$ (where $R^{16}$ is as defined above), or $R^5$ is $NH_2$ or $NR^{15}R^{16}$ (where $R^{15}$ and $R^{16}$ are as defined above); or $R^5$ is (optionally substituted) $C_{1-4}$ alkyl, $C_{3-6}$ cycloalkyl, $C_{2-4}$ alkynyl, or $C_{2-4}$ alkenyl; or $R^5$ is $S(O)_nR^{16}$, where $R^{16}$ is as defined above and n=0, 1, or 2;

$R^6$ is H, or (optionally substituted) $C_{1-8}$ alkyl, $C_{3-6}$ cycloalkyl, $C_{2-8}$ alkenyl, $C_{2-8}$ alkynyl, $C_{6-10}$ aryl or heterocycle;

$R^8$ is H, halogen, azido, cyano, thiocyano, =O, OH, $OR^{16}$ (where $R^{16}$ is as defined above); or $R^8$ is $NH_2$ or $NR^{15}R^{16}$ (where $R^{15}$ and $R^{16}$ are as defined above); or $R^8$ is (optionally substituted) $C_{1-18}$ alkyl, $C_{3-6}$ cycloalkyl, $C_{2-18}$ alkynyl, $C_{2-18}$ alkenyl, $C_{6-10}$ aryl or heterocycle; or $R^8$ is $COOR^{18}$ where $R^{18}$ is (optionally substituted) $C_{1-4}$ alkyl, $C_{3-6}$ cycloalkyl, $C_{2-4}$ alkenyl, $C_{2-4}$ alkynyl, $C_{6-10}$ aryl, or heterocycle; or $R^8$ is $S(O)_nR^{16}$, where $R^{16}$ is as defined above and n=0, 1, or 2;

$R^9$ is H, cyano, azido, halogen, thiocyano, OH, $OR^{16}$, where $R^{16}$ is as described above, or $R^9$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle; 2-heterocycle-substituted ethynyl, heterocycle-substituted $C_{1-4}$ alkyl, heterocycle-substituted $C_{2-4}$-alkenyl, heterocycle-substituted $C_{3-6}$ cycloalkyl; and $R^{10}$ is H, keto, halogen, cyano, thiocyano, azido or $NR^{15}R^{16}$, where $R^{15}$ and $R^{16}$ are as described above; or $R^{10}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl or heterocycle; or $R^{10}$ is $OR^{16}$ where $R^{16}$ as described above or $R^{16}$ is trimethylsilyl or triethylsilyl; or $R^{16}$ is =$CH_2$ or =$CHR^{19}$, where $R^{190}$ is (optionally substituted) $C_{1-4}$ alkyl, $C_{3-6}$ cycloalkyl, $C_{2-4}$ alkynyl, $C_{2-4}$ alkenyl or $C_{6-10}$ aryl; or $R^{10}$ is $S(O)_nR^{16}$, where $R^{16}$ is as defined above and n=0, 1, or 2; and stereoisomers and pharmaceutically acceptable compositions thereof.

In another embodiment of the present invention, the group $R^1$ as it appears in structure 2 is H or (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle, 2-heterocycle-substituted ethynyl, heterocycle-substituted $C_{1-4}$ alkyl, heterocycle-substituted $C_{2-4}$-alkenyl, heterocycle-substituted $C_{3-6}$ cycloalkyl wherein m=0, 1, or 2;

$R^2$ is OH or $OR^{14}$, where $R^{14}$ is HCO— or (optionally substituted) $C_{1-18}$ alkyl-CO— (except that $R^{14}$ is not $CH_3$ when $R^1$, $R^2$, $R^3$, $R^5$, $R^6$, $R^8$, $R^9$ and $R^{10}$=H, $R^4$=$CH_3$, and there are no double bonds present), $C_{2-18}$ alkenyl-CO—, $C_{2-18}$ alkynyl-CO—, $C_{6-10}$aryl-CO— or heterocycle-CO—; or $R^{14}$ is $C_{1-18}$ alkyl-X—CO—, $C_{2-18}$ alkenyl-X—CO—, $C_{2-18}$ alkynyl-X—CO—, aryl-X—CO— or heterocycle-X—CO—, where X is O or NH; or $R^{14}$ is trimethylsilyl or triethylsilyl; or $R^{14}$ is (optionally substituted) $C_{1-4}$ alkyl, $C_{3-6}$ cycloalkyl, $C_{2-4}$ alkynyl, or $C_2$-4 alkenyl; or $R^{14}$ is HO—$SO_2$— or a salt thereof; or $R^2$ is $NR^{15}R^{16}$, where $R^{15}$ is H, OH or (optionally substituted) $C_{1-4}$ alkyl, $C_{3-6}$ cycloalkyl, $C_{2-4}$ alkynyl, $C_{2-4}$ alkenyl, $C_{6-10}$ aryl, heterocycle, or $R^{15}$ is $OR^{17}$, where $R^{17}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, $C_{1-18}$ alkyl-CO—, $C_{2-18}$ alkenyl-CO—, $C_{2-18}$ alkynyl-CO—, $C_{6-10}$ aryl-CO— or heterocycle-CO—; and where $R^{16}$ is H or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, or $R^{16}$ is H—CO— or (optionally substituted) $C_{1-18}$ alkyl-CO—, $C_{2-18}$ alkenyl-CO—, $C_{2-18}$ alkynyl-CO—, $C_{3-6}$ cycloalkyl-CO—, $C_{6-10}$ aryl-CO— or heterocycle-CO— or $R^{16}$ is $C_{1-18}$ alkyl-X—CO—, $C_{2-18}$ alkenyl-X—CO—, $C_{2-18}$ alkynyl-X—CO—, aryl-X—CO— or heterocycle-X—CO—, where X is O or NH; wherein m=0, 1, or 2;

$R^3$ is H, halogen, cyano, azido or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle; wherein m=0, 1, or 2;

$R^4$ is H or (optionally substituted) Me; wherein m=0, 1, or 2;

$R^5$ is H, halogen, azido, cyano, thiocyano, =O, OH, $OR^{16}$ (where $R^{16}$ is as defined above), or $R^5$ is $NH_2$ or $NR^{15}R^{16}$ (where $R^{15}$ and $R^{16}$ are as defined above); or $R^5$ is (optionally substituted) $C_{1-4}$ alkyl, $C_{3-6}$ cycloalkyl, $C_{2-4}$ alkynyl, or $C_{2-4}$ alkenyl; or $R^5$ is $S(O)R^{16}$, where $R^{16}$ is as defined above and n=0, 1, or 2; wherein m=0, 1, or 2;

$R^6$ is H, or (optionally substituted) $C_{1-8}$ alkyl, $C_{3-6}$ cycloalkyl, $C_{2-8}$ alkenyl, $C_{2-8}$ alkynyl, $C_{6-10}$ aryl or heterocycle; wherein m=0, 1, or 2;

$R^7$ is H, cyano or (optionally substituted) $C_{1-8}$ alkyl, $C_{3-6}$ cycloalkyl, $C_{2-8}$ alkenyl, $C_{2-8}$ alkynyl, $C_{6-10}$ aryl or heterocycle; wherein m=0, 1, or 2;

$R^8$ is H, halogen, azido, cyano, thiocyano, =O, OH, $OR^{16}$ (where $R^{16}$ is as defined above); or $R^8$ is $NH_2$ or $NR^{15}R^{16}$ (where $R^{15}$ and $R^{16}$ are as defined above); or $R^8$ is (optionally substituted) $C_{1-18}$ alkyl, $C_{3-6}$ cycloalkyl, $C_{2-18}$ alkynyl, $C_{2-18}$ alkenyl, $C_{6-10}$ aryl or heterocycle; or $R^8$ is $COOR^{18}$ where $R^{18}$ is (optionally substituted) $C_{1-4}$ alkyl, $C_{3-6}$ cycloalkyl, $C_{2-4}$ alkenyl, $C_{2-4}$ alkynyl, $C_{6-10}$ aryl, or heterocycle; or $R^8$ is $S(O)_nR^{16}$, where $R^{16}$ is as defined above and n=0, 1, or 2; wherein m=0, 1, or 2;

$R^9$ is H, cyano, azido, halogen, thiocyano, OH, $OR^{16}$, where $R^{16}$ is as described above, or $R^9$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle; 2-heterocycle-substituted ethynyl, heterocycle-substituted $C_{1-4}$ alkyl, heterocycle-substituted $C_{2-4}$-alkenyl, heterocycle-substituted $C_{3-6}$ cycloalkyl; wherein m=0, 1, or 2; and $R^{10}$ is H, keto, halogen, cyano, thiocyano, azido or $NR^{15}R^{16}$, where $R^{15}$ and $R^{16}$ are as described above; or $R^{10}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl or heterocycle; or $R^{10}$ is $OR^{16}$ where $R^{16}$ as described above or $R^{16}$ is trimethylsilyl or triethylsilyl; or $R^{16}$ is $=CH_2$ or $=CHR^{19}$, where $R^{19}$ is (optionally substituted) $C_{1-4}$ alkyl, $C_{3-6}$ cycloalkyl, $C_{2-4}$ alkynyl, $C_{2-4}$ alkenyl or $C_{6-10}$ aryl; or $R^{10}$ is $S(O)_nR^{16}$, where $R^{16}$ is as defined above and n=0, 1, or 2; wherein m=0, 1, or 2 and stereoisomers and pharmaceutically acceptable compositions thereof.

In a further embodiment of the present invention, the group $R^1$ as it appears in structure 3 may be H or (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle; 2-heterocycle-substituted ethynyl, heterocycle-substituted $C_{1-4}$ alkyl, heterocycle-substituted $C_{2-4}$-alkenyl, heterocycle-substituted $C_{3-6}$ cycloalkyl;

$R^2$ group is OH or $OR^{14}$, where $R^{14}$ is HCO— or (optionally substituted) $C_{1-18}$ alkyl-CO— (except that $R^{14}$ is not $CH_3$ when $R^1$, $R^2$, $R^3$, $R^5$, $R^6$, $R^8$, $R^9$ and $R^{10}$=H, $R^4$=$CH_3$, and there are no double bonds present), $C_{2-18}$ alkenyl-CO—, $C_{2-18}$ alkynyl-CO—, $C_{6-10}$ aryl-CO— or heterocycle-CO—; or $R^{14}$ is (optionally substituted) $C_{1-18}$ alkyl-X—CO—, $C_{2-18}$ alkenyl-X—CO—, $C_{2-18}$ alkynyl-X—CO—, $C_{6-10}$ aryl-X—CO— or heterocycle-X—CO—; or $R^{14}$ is trimethylsilyl or triethylsilyl; or $R^{14}$ is (optionally substituted) $C_{1-4}$ alkyl, $C_{3-6}$ cycloalkyl, $C_{2-4}$ alkenyl, or $C_{2-4}$ alkynyl, or; or $R^{14}$ is HO—$SO_2$— or a salt thereof or $R^2$ is $NR^{15}R^{16}$, where $R^{15}$ is H, OH or (optionally substituted) $C_{1-4}$ alkyl, $C_{3-6}$ cycloalkyl, $C_{2-4}$ alkynyl, $C_{2-4}$ alkenyl, $C_{6-10}$ aryl, heterocycle or $R^{15}$ is $OR^{17}$, where $R^{17}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, $C_{1-18}$ alkyl-CO—, $C_{2-18}$ alkenyl-CO—, $C_{2-18}$ alkynyl-CO—, $C_{6-10}$ aryl-CO— or heterocycle-CO—; and where $R^{16}$ is H or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, or $R^{16}$ is H—CO— or (optionally substituted) $C_{1-18}$ alkyl-CO—, $C_{2-18}$ alkenyl-CO—, $C_{2-18}$ alkynyl-CO—, $C_{3-6}$ cycloalkyl-CO—, $C_{6-10}$ aryl-CO— or heterocycle-CO—;

where X is O or $NR^{100}$, where $R^{100}$ is (optionally substituted) $C_{1-4}$ alkyl, $C_{3-6}$ cycloalkyl, $C_{2-4}$ alkenyl, $C_{2-4}$ alkynyl $C_{6-10}$ aryl or heterocycle; or X is $NOR^{110}$, where $R^{110}$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which may be optionally substituted; or X is (H, H), (H, OH), (H, alkyl)$_3$), or (H, $OCOR^{111}$), where $R^{111}$ is $C_{1-6}$ alkyl, $C_{3-8}$ cycloalkyl, $C_{2-6}$ alkynyl, $C_{6-12}$ aryl, aralkyl, aralkenyl, aralkynyl, heteroaryl, heteroaralkyl, heteroaralkenyl or heteroaralkynyl, any of which may be optionally substituted; or X is

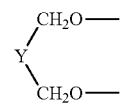

where Y is —$(CH_2)_m$— where m is an integer of 0 to 3, or Y is —$(CH_2)_n$—Z—$(CH_2)_p$— where n is an integer of 0 to 2, p is an integer of 0 to 2 and Z is a heteroatom (optionally substituted) or Z is a carbon atom substituted with one or two $C_{1-6}$ alkyl groups;

$R^3$ is H, halogen, cyano, azido or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle;

$R^4$ is H or (optionally substituted) Me;

$R^6$ is H, or (optionally substituted) $C_{1-8}$ alkyl, $C_{3-6}$ cycloalkyl, $C_{2-8}$ alkenyl, $C_{2-8}$ alkynyl, $C_{6-10}$ aryl or heterocycle;

$R^8$ is H, halogen, azido, cyano, thiocyano, =O, OH, $OR^{16}$ (where $R^{16}$ is as defined above); or $R^8$ is $NH_2$ or $NR^{15}R^{16}$ (where $R^{15}$ and $R^{16}$ are as defined above); or $R^8$ is (optionally substituted) $C_{1-18}$ alkyl, $C_{3-6}$ cycloalkyl, $C_{2-18}$ alkynyl, $C_{2-18}$ alkenyl, $C_{6-10}$ aryl or heterocycle; or $R^8$ is $COOR^{18}$ where $R^{18}$ is (optionally substituted) $C_{1-4}$ alkyl, $C_{3-6}$ cycloalkyl, $C_{2-4}$ alkenyl, $C_{2-4}$ alkynyl, $C_{6-10}$ aryl, or heterocycle; or $R^8$ is $S(O)_nR^{16}$, where $R^{16}$ is as defined above and n=0, 1, or 2;

$R^9$ is H, cyano, azido, halogen, thiocyano, OH, $OR^{16}$, where $R^{16}$ is as described above, or $R^9$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle; 2-heterocycle-substituted ethynyl, heterocycle-substituted $C_{1-4}$ alkyl, heterocycle-substituted $C_{2-4}$-alkenyl, heterocycle-substituted $C_{3-6}$ cycloalkyl;

$R^{11}$ is $C_{1-18}$ alkyl, $C_{2-18}$ alkenyl, $C_{2-18}$ alkynyl, $C_{3-8}$ cycloalkyl, $C_{6-12}$ aryl, aralkyl, aralkenyl, aralkynyl, heteroaryl, heteroaralkyl, heteroaralkenyl or heteroaralkynyl any of which may by optionally substituted; or $R^{11}$ is

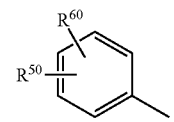

where $R^{50}$ and $R^{60}$ are each independently H; halogen; $(R^{70}R^{80}N(O)_r)$—, where r is 0 or 1 and $R^{70}$ and $R^{80}$ are each independently H, $C_{1-6}$ alkyl, $C_{3-8}$ cycloalkyl, $C_{2-6}$ alkenyl or $C_{2-6}$ alkynyl, any of which may be optionally substituted; substructure II,

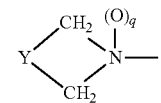

where q is 0 or 1, Y is —$(CH_2)_m$— where m is an integer of 0 to 5, or Y is —$(CH_2)_n$—Z—$(CH_2)_p$— where n is an integer of 0 to 2, p is an integer of 0 to 2, and Z is a heteroatom (optionally substituted) and where the $CH_2$ groups may be optionally substituted; N-imidazolyl; —N-pyrrolyl-; HO—; $CF_3SO_2$—; $C_{1-6}$ alkyl-O—; $C_{1-6}$ perfluoroalkyl-O—; $C_{1-6}$ alkyl-S—; $C_{1-6}$ alkyl-CH(OH)—; NC—; HCC—; $C_6H_5$CC—; 2'-furyl; 3'-furyl; 2'-thiophenyl; 3'-thiophenyl; 2'-pyridyl; 3'-pyridyl; 4'-pyridyl; 2'-thiazolyl; 2'-N-methylimidazolyl; 5'-pyrimidinyl; $C_6H_5$—; $H_2C$=CH—; $C_{1-6}$ alkyl; MeC(=$CH_2$)—; $C_{1-6}$ alkyl-CO; HCO; $C_{1-6}$ alkyl; C=$NOR^{120}$, or HC=$NOR^{120}$, where $R^{120}$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which may be optionally substituted; or $R^{50}$ and $R^{60}$ combine to form a ring

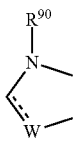

where W is $CH_2$, CH, NH, N, O, or S, and $R^{90}$ is H or $C_{1-6}$ alkyl; or $R^{50}$ and $R^{60}$ combine to form a ring

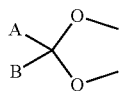

where A and B are each independently H, F or $C_{1-6}$ alkyl or A and B combine to form =O; or $R^{50}$ and $R^{60}$ combine to form a ring

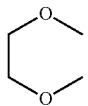

where the $CH_2$ groups may be independently and optionally substituted; and $R^{13}$ is one of hydrogen, thio-$C_{1-4}$-alkyl, thio-$C_{2-4}$-alkenyl, nitro, cyano, $C_{1-4}$ alkoxy, substituted $C_{1-4}$ alkoxy, $C_{2-4}$ alkenyloxy, aminocarbonyl, mono-$C_{1-4}$-alkylaminocarbonyl, di-$C_{1-4}$-alkylaminocarbonyl, sulfinyl, sulfonyl, thio, sulfonamido, $C_{2-4}$-alkynyloxy, optionally substituted $C_{6-10}$ aryloxy, optionally substituted $C_{6-10}$ aryl-$C_{1-4}$-alkyloxy, an optionally substituted 1,3-dioxolan-4-one of an acetyl group, an optionally substituted 1,3-dioxan-4-one of an acetyl group, an optionally substituted 1,3-oxathiolan-5-one of an acetyl group, an optionally substituted 1,3-oxathian-5-one of an acetyl group, —O—C(O)—NR'R", —C(O)—$CH_2$-J-G, —C(O)—$CH_2$—O-T, —C(O)—$CH_2$—O-E, —C(O)—$CH_2$-Q-G, —C(O)—$CH_2$-J'-Q-G, or —C(O)—$CH_2$-J'-Q-L, wherein R' and R" independently represent hydrogen or optionally substituted $C_{1-4}$ alkyl, or taken together with the nitrogen to which they are attached form a 3- to 6-membered heterocyclic ring;

J is one of S, SO or $SO_2$;

J' is one of O, S, SO or $SO_2$;

Q is one of $C_{1-4}$ alkyl, $C_{2-4}$ alkenyl or $C_{2-4}$ alkynyl;

G is one of C-attached hetero-$C_{5-10}$-aryl, optionally substituted $C_{6-10}$ aryl, a quaternary ammonium salt of a nitrogen containing hetero-$C_{6-10}$-aryl group or a quaternary salt of an amino substituted $C_{6-10}$ aryl group;

T is C-attached hetero-$C_{5-10}$-aryl or a quaternary ammonium salt of a nitrogen containing hetero-$C_{5-10}$-aryl group;

E is optionally substituted $C_{6-10}$ aryl or a quaternary ammonium salt of an amino substituted $C_{6-10}$ aryl group;

L is one of amino, amido, cyano, thiocyano, azido, nitro, hydroxy, halo, carboxyl, $C_{1-4}$ alkoxy, $C_{1-4}$ alkoxycarbonyl, $C_{1-4}$ alkanoyloxy, hydrogen, sulfate, thiosulfate, sulfonate, $C_{1-4}$ alkylthio, $C_{1-4}$ alkylsulfinyl, $C_{1-4}$ alkylsulfonyl or mercapto.

Specific Non-Limiting Examples Include the Compounds:

17β-Nitro-5α-androstan-3α-ol; 3α-Hydroxy-3β-methyl-17β-nitro-5α-androstane; 3α-Hydroxy-17β-thiomethyl-5α-androstane; 11β-[4-(N,N-Dimethylamino)phenyl]-3α-hydroxy-3β-methyl-17β-nitro-5α-estrane; 3β-Hydroxy-5α-androstan-17-oxime; 17β-Nitro-5α-androstan-3β-ol; 17β-Nitro-21-nor-23-oxo-17α-cholan-3α-ol; 5'-Methylspiro-[androstan-17β, N-oxido-2'-pyrrolidine]-3α-ol; 5'-Methylspiro-[androstan-17β, 2'-pyrrolidine]-3α-ol; 1'-Formyl-5-methylspiro-[androstan-17β, 2'-pyrrolidine]-3α-ol; 17β-Nitro-5α-androstan-3α-ol benzoyl ester; 17β-Amino-5α-androstan-3α-ol benzoyl ester; 17β-(Acetylamino)-5α-androstan-3α-ol benzoyl ester; 17β-(Acetylamino)-5α-androstan-3α-ol; 17β-[1-Oxopropyl)-amino]-5α-androstan-3α-ol benzoyl ester; 17β-[(1-Oxopropyl)-amino]-5α-androstan-3α-ol; 17β-(N-Oxido-2-propaneimine)-5α-androstan-3α-ol; 3α-Hydroxy-5α-androstan-17-thione; 3α-Hydroxy-5α-androstan-17β-thiol; 3α-Hydroxy-5α-androstan-17β-methylsulfoxide (both diastereomers); 3α-Hydroxy-5α-androstan-17β-methylsulfone; 3α-Hydroxy-17-(2-furanyl)-5α-androst-16-ene; 3α-Hydroxy-17β-(2-furanyl)-5α-androstane; 11β-[4-(N,N-Dimethylamino)phenyl]-3α-hydroxy-3β-methyl-5α-17β-hydroxy-estrane hydrochloride; 11β-[4-(N,N-Dimethylamino)phenyl]-3α-hydroxy-3β-methyl-5α-estra-17-one hydrochloride; 11β-[4-(N,N-Dimethylamino)phenyl]-3α-hydroxy-3β-methyl-5α-estrane-17-oxime; 11β-[4-(N,N-Dimethyl-N-(oxy)amino)phenyl]-3α-hydroxy-3β-methyl-5α-estrane-17-oxime; 3α-Amino-5α-androstan-17-one; 3α-Amino-17β-nitro-5α-androstane hydrochloride; 3α-Dimethylamino-17β-nitro-5α-androstane hydrochloride; 3α-N-Hexylamino-17β-nitro-5α-androstane hydrochloride; 3α-N-(3-Phenylpropyl)-17β-nitro-5α-androstane hydrochloride; 3α-Acetamido-5α-17β-nitro-androstane.

Those compounds of the present invention, which bear an amino group, may also comprise a salt formed with the amine. Suitable pharmaceutically acceptable salts are known to those of ordinary skill in the art comprise carboxylates, sulfates, phosphates and halides.

The compounds of the present invention may be administered by a variety of methods. Thus, those products of the invention that are active by the oral route may be administered in solutions, suspensions, emulsions, tablets, including sublingual and intrabuccal tablets, soft gelatin capsules, including solutions used in soft gelatin capsules, aqueous or oil suspensions, emulsions, pills, lozenges, troches, tablets, syrups or elixirs and the like. Products of the invention active on parenteral administration may be administered by depot injection, implants including SILASTIC™ and biodegradable implants, skin patches, skin creams, or intramuscular and intravenous injections.

Compositions may be prepared according to any method known to the art for the manufacture of pharmaceutical compositions and such compositions may contain one or more agents selected from the group consisting of sweetening agents, flavoring agents, coloring agents and preserving agents. Tablets containing the active ingredient in admixture with nontoxic pharmaceutically acceptable excipients which are suitable for manufacture of tablets are acceptable. These excipients may be, for example, inert diluents, such as calcium carbonate, sodium carbonate, lactose, calcium phosphate or sodium phosphate granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatin capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol (e.g., polyoxyethylene sorbitol mono-oleate), or a condensation product of ethylene oxide with a partial ester derived from a fatty acid and a hexitol anhydride (e.g., polyoxyethylene sorbitan mono-oleate). The aqueous suspension may also contain one or more preservatives such as ethyl or n-propyl p-hydroxybenzoate, one or more coloring agents, one or more flavoring agents and one or more sweetening agents, such as sucrose, aspartame or saccharin. Ophthalmic formulations, as is known in the art, will be adjusted for osmotic pressure.

Oil suspensions may be formulated by suspending the active ingredient in a vegetable oil, such as *arachis* oil, olive oil, sesame oil or coconut oil, or in a mineral oil such as liquid paraffin. The oil suspensions may contain a thickening agent, such as beeswax, hard paraffin or cetyl alcohol. Sweetening agents may be added to provide a palatable oral preparation. These compositions may be preserved by the addition of an antioxidant such as ascorbic acid.

Dispersible powders and granules of the invention suitable for preparation of an aqueous suspension by the addition of water may be formulated from the active ingredients in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, may also be present.

The pharmaceutical composition of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylenesorbitan mono-oleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a nontoxic parenterally acceptable diluent or solvent, such as a solution of 1,3-butanediol. Among the acceptable vehicles and solvents that may be employed are water and Ringer's solution, an isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Sterilization may be performed by conventional methods known to those of ordinary skill in the art such as, for example, by aseptic filtration, or irradiation.

Aqueous formulations (i.e oil-in-water emulsions, syrups, elixirs and injectable preparations) may be formulated to achieve the pH of optimum stability. The determination of the optimum pH may be performed by conventional methods known to those of ordinary skill in the art. Suitable buffers may also be used to maintain the pH of the formulation.

The compounds of this invention may also be administered in the form of suppositories for rectal administration of the drug. These compositions can be prepared by mixing the drug with a suitable nonirritating excipient which is solid at ordinary temperatures but liquid at rectal temperatures and will therefore melt in the rectum to release the drug. Non-limiting examples of such materials are cocoa butter and polyethyleneglycols.

They may also be administered by intranasal, intraocular, intravaginal, and intrarectal routes including suppositories, insufflation, powders and aerosol formulations.

Products of the invention which are preferably administered by the topical route may be administered as applicator sticks, solutions, suspensions, emulsions, gels, creams, ointments, pastes, jellies, paints, powders, and aerosols.

The compounds according to the present invention may be administered to any warm-blooded mammal such as humans, domestic pets, and farm animals. Domestic pets include dogs, cats, etc. Farm animals include cows, horses, pigs, sheepgoats, etc.

The amount of active ingredient that may be combined with a carrier material to produce a single dosage form will vary depending upon the disease treated, the mammalian species, and the particular mode of administration. A therapeutically effective amount may be determined by routine experimentation and by analogy from the amounts used to treat the same disease states with analogous steroid compounds. For example, a unit dose of the steroid may preferably contain between 0.1 milligram and 1 gram of the active ingredient. A more preferred unit dose is between 0.001 and 0.5 grams. It will be understood, however, that the specific dose level for any particular patient will depend on a variety of factors including the activity of the specific compound employed; the age, body weight, general health, sex and diet of the individual being treated the time and route of administration; the rate of excretion: other drugs which have previously been administered; and the severity of the particular disease undergoing therapy, as is well understood by those of skill in the art.

Figure 4:
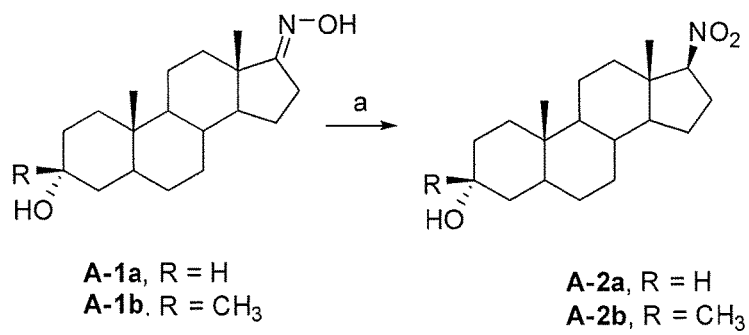
FIG. 4 provides a synthetic scheme for the preparation of compounds A1-A2.
Figure 5:
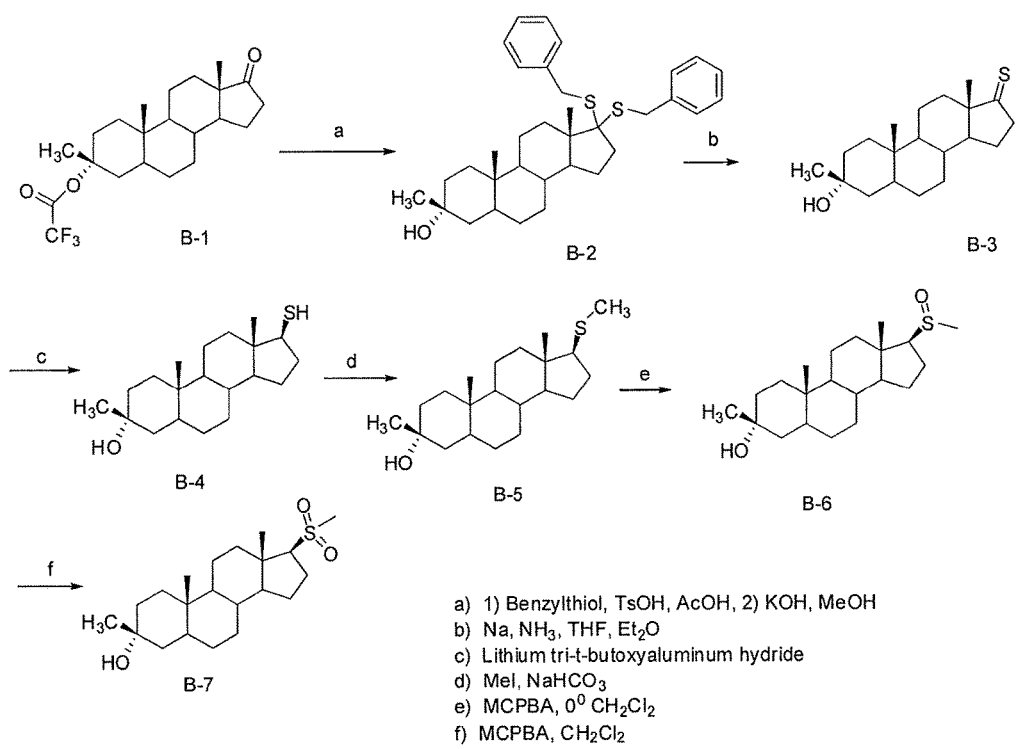
FIG. 5 provides a synthetic scheme for the preparation of compounds B1-B7.
Figure 6:
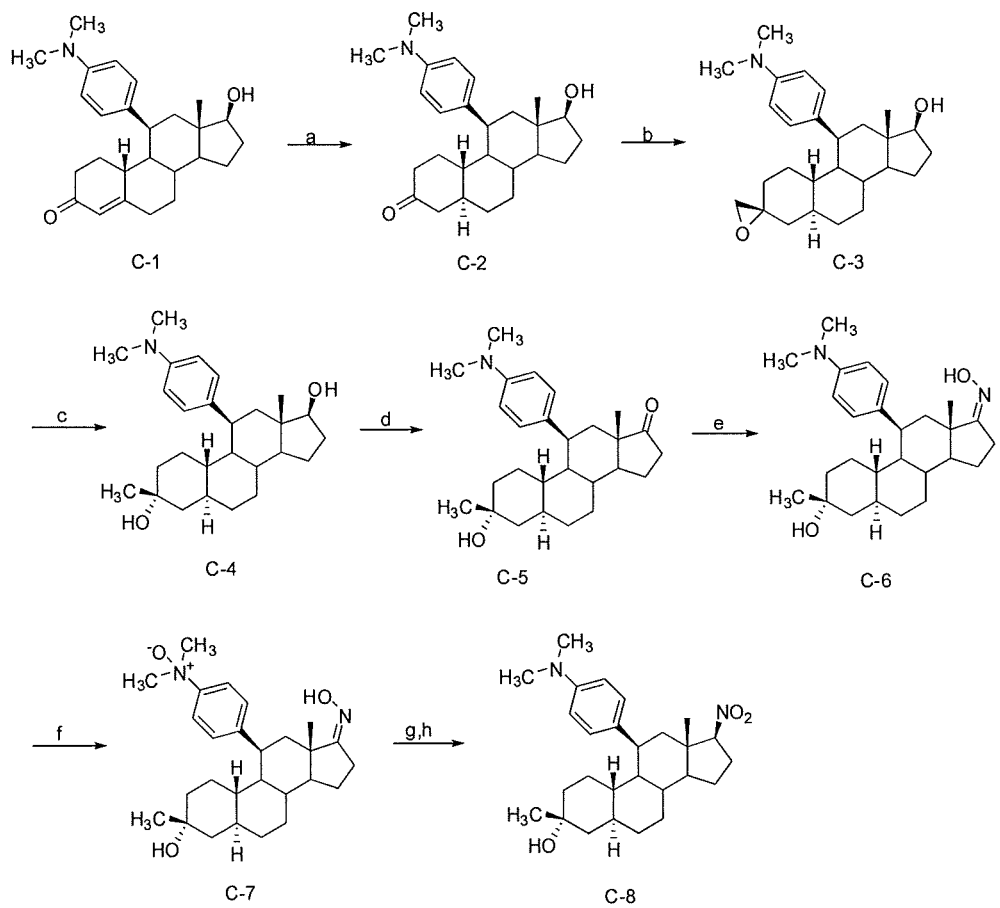
FIG. 6 provides a synthetic scheme for the preparation of compounds C1-C8.

Compounds of the invention may be made according to the procedures outlined in FIGS. 4, 5 and 6. Compounds of type A-2a,b where R═H or $CH_3$ may be prepared from the requisite oxime (J. Med. Chem 2000, 3201-3204) A-1a,b by using N-bromosuccinimidein dioxane water followed by sodium borohydride according to the method of Patchett et al. (Patchett, A. A., Hoffman, F., Giarrusso, F. F., Schwam, H. and Arth, G. E., 1962, The Synthesis of 17β-Amino-17α-(2'-carboxyethyl)androstane Lactams, J Org. Chem. 27, 3822). (see FIG. 4)

Compounds of type B-1-B-7 where prepared by treating 3β-methyl-3α-trifluoroacetoxy-5α-androstan-17-one with benzylthiol in acetic acid/toluenesulfonic acid followed by ester cleavage with potassium hydroxide in methanol according to the method of Swann et al. (Swann, D. A.; Turnbull, J. H.; TETRAB; Tetrahedron; EN; 24; 1968; 1441-1444) The resulting bisbenzylthio B-2 is cleaved to thione B-3 using sodium in liquid ammonia. Reduction of thione B-3 to provide the 17β-thiol B-4 is accomplished with lithium tritertbutoxyaluminumhydride. Treatment of B-4 with methyl iodide accomplishes selective alkylation providing B-5. Subsequent oxidation with metachloroperbenzoic acid at 0° C. in dichloromethane provided diastereomeric sulfoxides B-6 which were separated into their respective isomers using silica gel chromatography. Further oxidation with metachloroperbenzoic acid provided the sulfone B-7. (see FIG. 5)

Compounds C1-C8 were prepared from 11β-[4-(N,N-dimethylamino)phenyl]-17β-hydroxy-5α-estr-4-ene-3-one (Cleve, Arwed; Scheidges, Cornelius; Neef, Guenter; Ottow, Eckhard; Elger Walter; Beier, Sybille. Preparation of 11-β-aryl-4-estrenes as antiestagens and antiglucocorticoids, EP 404283). Compound C-1 was treated with lithium metal in liquid ammonia to provide C-2 in moderate yield. Stereospecific addition of sodium trimethylsulfoxonium iodide to C-2 provided epoxide C-3 according to the method of Cook and colleagues. (Cook, C. E., R. C. Corley and M. E. Wall (1968). Steroids. LXXIX. Synthesis and reactions of oxiranes obtained from 3- and 17-keto steroids. J. Org. Chem. 33(7): 2789-2793). Ring opening of C-3 with lithium aluminum hydride in tetrahydrofuran provided C-4 in excellent yield. Oxidation of C-4 with tetrapropylammonium perruthenate followed by treatment with hydroxylamine hydrochloride in pyridine gave oxime C-6 in moderate yield. The aniline group in C-6 was protected as the N-oxide using metachloroperbenzoic acid in dichloromethane. The final oxidation was carried out using N-bromosuccinimide followed by sodium borohydride dioxane water according to the method of Patchett et al. (Patchett, A. A., Hoffman, F., Giarrusso, F. F., Schwam, H. and Arth, G. E., 1962, The Synthesis of 17β-Amino-17α-(2'-carboxyethyl)androstane Lactams, J Org. Chem. 27, 3822). Deprotection of the N-oxide with ferric sulfate in water provided the target molecule C-8 in moderate yield. (see FIG. 6)

Having generally described this invention, a further understanding can be obtained by reference to certain specific examples which are provided herein for purposes of illustration only and are not intended to be limiting unless otherwise specified.

EXAMPLES

Synthetic Methods

Unless otherwise stated, reagent-grade chemicals and anhydrous solvents were obtained from commercial sources and were used without further purification. All moisture and air-sensitive reactions and reagent transfers were carried out under dry nitrogen or argon. Thin layer chromatography (TLC) was performed on EM Science precoated silica gel 60F-254 plates. Compounds were normally visualized by UV light (254 nm) or p-anisaldehyde spray. Preparative column chromatography employed EM Science silica gel, 60 Å (230-400 mesh). Solutions were concentrated by use of a rotary evaporator under water aspirator pressure at ambient temperature. Melting points were taken on a Mel-Temp II and are uncorrected. Unless otherwise noted, $^1$H NMR spectra were obtained at 300 MHz on a Brucker Avance 300 spectrometer in CDCl3 as solvent with tetramethylsilane (TMS) as internal standard. Chemical shifts are reported in units of ppm downfield from TMS. Mass spectra were normally obtained by electron impact at 70 eV on a Hewlett Packard 5989A instrument. Elemental analyses were performed by Atlantic Microlab Inc., Atlanta, Ga.

Example 1

Synthesis of 17β-Nitro-5α-androstan-3α-ol

3α-(t-butyldimethylsiloxy)-5α-androstan-17-oxime

Hydroxylamine hydrochloride (2 g, 29 mmol) was added to 3α-(t-butyldimethylsiloxy)-5α-androstan-17-one (approx. 13 mmol) in anhydrous pyridine (200 mL). The solution was allowed to stir at room temperature for 14 h and concentrated under reduced pressure. The resulting oil was purified on silica using medium pressure column chromatography (hexane/EtOAc, 7:3 and 3α-(t-butyldimethylsiloxy)-5α-androstan-17-oxime (4.85 g, 88%) was collected and isolated as a shiny, white solid. $^1$H-NMR (300 MHz, $CDCl_3$) δ 0.01, (s, 6H), 0.76 (s, 3H), 0.87 (s, 9H), 0.88 (s, 3H), 1.89-1.16 (m, 22H), 2.55-2.46 (m, 2H), 3.94 (s, 1H).

3α-(t-butyldimethylsiloxy)-17β-nitro-5α-androstane

A solution of $KHCO_3$ (5.8 g, 57 mmol) in $H_2O$ (60 mL) was added to a solution of NBS (5.1 g, 29 mmol) in dioxane (50 mL). The suspension was allowed to stir at room temperature for 0.25 h and 3α-(t-butyldimethylsiloxy)-5αandrostan-17-oxime (4.0 g, 9.5 mmol) in dioxane (150 mL) was added in a dropwise manner. A pale green color rapidly developed, and the reaction was allowed to stir at room temperature for 10 h. The solution was cooled to 0° C. and $NaBH_4$ (2.66 g, 67 mmol) was added in portions. A large amount of gas evolution was observed and the reaction was allowed to stir overnight, gradually warming to room temperature. The reaction was quenched with saturated aqueous $NH_4Cl$ (50 mL) and concentrated to ¼ its original volume. The resulting suspension was partitioned between water (100 mL) and EtOAc (200 mL), and the layers were separated. The aqueous layer was then extracted with EtOAc (3×100 mL) and organic extracts combined, washed with brine (100 mL), dried ($Na_2SO_4$), and concentrated under reduced pressure. The resulting oil was purified on silica using medium pressure column chromatography (hexane/EtOAc. 6:4). The solid product (3.36 g, 84%) was collected and used without further purification. $^1$H-NMR (300 MHz, CDCl$_3$) δ 0.01 (s, 6H), 0.72 (s, 3H), 0.82 (s, 3H) 0.88 (s, 9H), 2.03-0.89 (m, 23H), 2.67-2.41 (m, 1H), 3.94 (br s, 1H), 4.35 (dd, J=9.9 Hz, 1H).

17β-nitro-5α-androstan-3α-ol

Aqueous HCl (1 M, 20 mL) was added to a suspension of 3α-(t-butyldimethylsiloxy)-17β-nitro-5αandrostane (2.89 g, 6.6 mmol) in methanol (100 mL) and was allowed to stir overnight at room temperature. The reaction mixture was concentrated under reduced pressure, partitioned between EtOAc (100 mL) and brine (50 mL), and the layers were separated. The aqueous fraction was then extracted with EtOAc (2×50 mL) and the organic extracts were combined, washed with saturated aqueous NaHCO$_3$ (50 mL), brine (50 mL), dried over (Na$_2$SO$_4$), and concentrated under reduced pressure. The resulting semisolid was purified on silica using medium pressure column chromatography (hexane/EtOAc, 7:3) to provide 17β-nitro-5α-androstan-3α-ol (1.05 g, 49%) as a pale yellow solid. $^1$H-NMR (300 MHz, CDCl$_3$) δ 0.73 (s, 3H), 0.79 (s, 3H), 2.05-0.86 (m, 23H), 2.70-2.52 (m, 1H), 4.05 (br s, 1H), 4.37 (dd, J=9, 9 Hz, 1H).

Example 2

Synthesis of 3α-Hydroxy-3β-methyl-17β-nitro-5α-androstane

3-Hydroxy-3β-methyl-17β-nitro-5α-androstane

KHCO$_3$ (0.55 g, 5.46 mmol) in H$_2$O (20 mL) was added to a well stirred solution of NBS (0.50 g, 2.73 mmol) in dioxane (40 mL). The suspension was allowed to stir at room temperature for 0.25 h and a solution of 3β-methyl-3α-hydroxy-5α-androstan-17-oxime (0.29 g, 0.91 mmol) in dioxane (40 mL) was added. The blue solution was allowed to stir for 10 h at room temperature and was then cooled to 0° C. NaBH$_4$ (0.25 g, 6.83 mmol) was then added cautiously. After 3 h, H$_2$O (100 mL) was added and the slurry was extracted with CH$_2$Cl$_2$ (3×100 mL). The organic extracts were combined, dried (MgSO$_4$) and concentrated under reduced pressure to provide a white solid. The solid was purified on silica using medium pressure column chromatography (petroleum ether/acetone, 8.5:1.5). The resulting white solid was recrystallized from EtOAc/hexane to provide white needles (0.10 g, 33%). mp. 211-213° C. $^1$H-NMR (300 MHz, CDCl$_3$) δ 0.72 (s, 3H), 0.76 (s, 3H), 0.79-1.75 (m, 25H), 2.03-2.08 (m, 2H), 2.48-2.58 (m, 1H), 4.34-4.40 (dd, J=9.9 Hz, 1H). Elemental Anal. for C$_{20}$H$_{33}$NO$_3$ Calcd. C: 71.6, H: 9.91, N: 4.17. Found. C: 71.71, H: 9.97, N: 4.21. Ref for oxime. *J. Med. Chem* 2000, 3201-3204

Example 3

Synthesis of 3α-Hydroxy-17β-thiomethyl-5α-androstane 17,17-Bisbenzylthio-5α-androstane-3α-ol Toluenesulfonic acid (0.27 g, 1.43 mmol) was added to a well stirred solution of benzyl mercaptan (2.41 g, 19.4 mmol) and 3α-trifluoro acetoxy-5α-androstan-17-one (3.0 g, 7.76 mmol) in glacial AcOH (30 mL). The reaction was allowed to stir at room temperature for 18 h and was concentrated under reduced pressure. The resulting oil was taken up in 95% EtOH (140 mL) and 1N KOH (60 mL) was added. The slurry was then heated at reflux for 4 h, cooled, and diluted with H$_2$O (200 mL). The mixture was extracted with CH$_2$Cl$_2$ (3×250 mL) and the organic fractions were combined, dried (MgSO$_4$) and concentrated under reduced pressure. The resulting oil was purified on silica using medium pressure column chromatography (petroleum ether/acetone, 9:1) to provide a white solid. The white solid was recrystallized from EtOAc/petroleum ether to provide colorless needles (3.76 g, 93%). mp. 184-185° C. $^1$H-NMR (300 MHz, CDCl$_3$) δ 0.78 (s, 3H), 1.06 (s, 3H), 0.98-2.07 (m, 25H), 3.85-4.02 (m, 5H), 7.23-7.35 (m, 10H).
Ref: Swann et al. *Tetrahedron*, Vol 24 1441-1444 1968

3α-hydroxy-5α-androstan-17-thione 17,17-Bisbenzylthio-5α-androstane-3α-ol (3.76 g, 7.22 mmol) in THF/Et$_2$O (40:100 mL) was added in a dropwise manner to a suspension of Na (3.32 g, 144.4 mmol) in liquid NH$_3$ at −78° C. under N$_2$. The blue suspension was allowed to stir at −78° C. for 3 h. The reaction was then quenched by the addition of saturated NH$_4$Cl (50 mL) and H$_2$O (150 mL). The resulting biphasic mixture was extracted with CH$_2$Cl$_2$ (3×200 mL). The extracts were combined, dried (MgSO$_4$), and concentrated to provide an orange semisolid. The semisolid was purified on silica using medium pressure column chromatography (petroleum ether/acetone, 8:2). The resulting solid was recrystallized from EtOAc/hexane to provide a salmon colored solid (1.06 g, 48%). mp. 172-173° C. $^1$H-NMR (300 MHz, CDCl$_3$) δ 0.82 (s, 3H), 0.89 (s, 3H), 0.90-1.68 (m, 21H), 1.99-2.03 (m, 2H), 2.59-2.69 (ddd, J=9, 9, 21 Hz, 1H), 2.90-3.00 (dd, J=9, 9 Hz, 1H), 4.06 (m, 1H). Elemental Anal. for C$_{19}$H$_{30}$OS Calcd. C: 74.45, H: 9.87, S: 10.46. Found. C: 74.33, H: 10.01, S: 10.47.

3α-hydroxy-5α-androstan-17β-thiol

A 1.0 M solution of lithium tri-t-butoxy aluminum hydride in THF (6.27 mL, 6.27 mmol) was added in a dropwise manner to a solution of 3α-hydroxy-5α-androstan-17-thione (0.64 g, 2.09 mmol) in THF (60 mL) at 0° C. under N$_2$. The solution was allowed to stir for 2 h at 0° C. and then another 2 h at room temperature. Saturated NaHCO$_3$ (75 mL) was added and the slurry was extracted with CH$_2$Cl$_2$ (3×100 mL). The organics were combined, dried (MgSO$_4$), and concentrated under reduced pressure. The resulting white solid was recrystallized from heptane to provide a white powder (0.61 g, 95%). mp. 169-170° C. $^1$H-NMR (300 MHz, CDCl$_3$) δ 0.70 (s, 3H), 0.79 (s, 3H), 0.80-1.70 (m, 23H), 2.16-2.18 (m, 2H), 2.58-2.69 (dd, J=9, 18 Hz, 1H), 2.90-3.00 (dd, J=9, 9 Hz, 1H), 4.06 (m, 1H). Elemental Anal. for C$_{19}$H$_{32}$OS Calcd. C: 73.97, H: 10.45, S: 10.39. Found. C: 73.82, H: 10.73, S: 10.28.

3α-Hydroxy-17β-thiomethyl-5α-androstane

Methyl iodide (0.35 g, 2.48 mmol) was added to a well stirred suspension of 3α-hydroxy-5α-androstan-17β-thiol (0.61 g, 1.98 mmol) and K$_2$CO$_3$ (1.38 g, 10 mmol) in anhydrous DMF (50 mL). The suspension was allowed to stir at room temperature for 4 h and H$_2$O (100 mL) was added. The biphasic mixture was extracted with CH$_2$Cl$_2$ (3×150 mL) and the organics were combined, dried (MgSO$_4$) and concentrated under reduced pressure. The resulting solid was purified on silica using medium pressure column chromatography (petroleum ether/acetone, 9:1) to afford a white solid. The solid was recrystallized from heptane to provide a white powder (0.19 g, 30%). mp. 151-153° C. $^1$H-NMR (300 MHz, CDCl$_3$) δ 0.74 (s, 3H), 0.79 (s, 3H), 0.80-1.55 (m, 23H), 1.63-1.69 (m, 1H), 2.11 (m, 4H), 2.51-2.57 (dd, J=9, 9 Hz, 1H), 4.05 (m, 1H). Elemental Anal. for C$_{20}$H$_{34}$OS Calcd. C: 74.47, H: 10.62, S: 9.94. Found. C: 74.26, H: 10.81, S: 9.89.

Example 4

Synthesis of (+) and (−)3α-Hydroxy-5α-androstan-17β-methylsulfoxide (+) and (−)3α-Hydroxy-5α-androstan-17β-methylsulfoxide MCPBA (0.16 g, 0.71 mmol, 77%) was added at 0° C. to a solution of 3α-hydroxy-17β-thiomethyl-5α-androstane (0.19 g, 0.59 mmol) in CH$_2$Cl$_2$ (100 mL). The solution was allowed to stir for 0.5 h at 0° C. and saturated NaHCO$_3$ (50 mL) was added. The biphasic mixture was extracted with CH$_2$Cl$_2$ (3×100 mL) and the organics were combined, dried (MgSO$_4$) and concentrated under reduced pressure. The resulting semisolid was purified on silica using medium pressure column chromatography (Et$_2$O/acetone, 9:1) to provide 0.050 g of each diatereomers and ≈0.075 g mixed fractions.

Top spot (11474-36t). The solid was recrystallized from EtOAc/hexane to provide 3α-Hydroxy-5α-androstan-17β-methylsulfoxide as colorless needles (0.50 g, 50%). mp. 245-247° C. $^1$H-NMR (500 MHz, CDCl$_3$) δ 0.79 (s, 3H), 0.87 (s, 3H), 0.80-1.95 (m, 24H), 2.30-2.33 (dd, J=9, 9, Hz, 1H), 2.37-2.44 (m, 1H), 2.49 (s, 3H), 4.05 (m, 1H). Elemental Anal. for C$_{20}$H$_{34}$O$_2$S Calcd. C: 70.96, H: 10.12, S: 9.47. Found. C: 70.86, H: 10.21, S: 9.44.

Bottom spot: The solid was recrystallized from EtOAc/hexane to provide 3α-Hydroxy-5α-androstan-17β-methylsulfoxide as colorless needles (0.50 g, 50%). mp. 251-253° C. $^1$H-NMR (500 MHz, CDCl$_3$) δ 0.79 (s, 3H), 1.03 (s, 3H), 0.98-2.41 (m, 24H), 2.48 (s, 3H), 2.59-2.63 (dd, J=9, 9 Hz, 1H), 4.05 (m, 1H). Elemental Anal. for C$_{20}$H$_{34}$O$_2$S Calcd. C: 70.96, H: 10.12, S: 9.47. Found. C: 70.77, H: 10.01, S: 9.40.

Example 5

Synthesis of 3α-Hydroxy-5α-androstan-17β-methylsulfone

Synthesis of 3α-Hydroxy-5α-androstan-17β-methylsulfone

MCPBA (0.10 g, 0.44 mmol) was added to a diatereomeric mixture of 3α-hydroxy-5α-androstan-17β-methylsulfoxide (0.075 g, 0.22 mmol) in CH$_2$Cl$_2$ (50 mL). The solution was allowed to stir at room temperature for 2 h, saturated NaHCO$_3$ was added (50 mL), and the biphasic mixture was extracted with CH$_2$Cl$_2$ (3×100 mL). The organics were combined, dried (MgSO$_4$) and concentrated under reduced pressure. The resulting solid was purified on silica using medium pressure column chromatography (acetone/petroleumether, 6:4). The product was collected and recrystallied from EtOAc/heptane to provide 3α-Hydroxy-5α-androstan-17β-methylsulfone as a white powder (0.061 g, 78%). mp. 223-226° C. $^1$H-NMR (300 MHz, CDCl$_3$) δ 0.79 (s, 3H), 1.04 (s, 3H), 0.80-2.32 (m, 25H), 2.80 (s, 3H), 2.86-2.93 (dd, J=9.6, 9.6 Hz, 1H), 4.13 (m, 1H). Elemental Anal. for C$_{20}$H$_{34}$O$_3$S.0.25H$_2$O Calcd. C: 66.90, H: 9.68, S: 8.93. Found. C: 67.05, H: 9.62, S: 8.79.

Example 6

Synthesis of 11β-[4-(N,N-Dimethylamino)phenyl]-3α-hydroxy-3β-methyl-5α-17β-nitro-estrane 11β-[4-(N,N-dimethylamino)phenyl]-5α-17β-hydroxy-estr-3-one Lithium metal (0.04 g, 6.35 mmol) was added to liquid NH$_3$ (40 mL) at −78° C. and allowed to stir for 15 min. Anhydrous THF (25 mL) was added and then a solution of anhydrous THF (25 mL), t-butanol (0.30 mL), and 11β-[4-(N,N-dimethylamino)phenyl]-5α-17β-hydroxy-estr-4-ene-3-one (1.0 g, 2.54 mmol) was rapidly added. The blue solution was allowed to stir at −78° C. for 5 min and then quenched with solid NH$_4$Cl. Saturated NH$_4$Cl (150 mL) was then added and the biphasic mixture was extracted with EtOAc (3×150 mL). The organic extracts were combined, dried (MgSO$_4$), and concentrated under reduced pressure. The resulting semisolid was purified on silica using medium pressure column chromatography (petroleum ether/acetone, 8.5:1.5) to provide 11β-[4-(N,N-dimethylamino)phenyl]-5α-17β-hydroxy-estr-3-one as a colorless semisolid (0.80 g, 80%). $^1$H-NMR (300 MHz, CDCl$_3$) δ 0.52 (s, 3H), 0.93-2.25 (m, 24H), 2.93 (s, 6H), 3.15 (m, 1H), 3.52 (dd, J=7.8, 7.8 Hz, 1H), 6.41 (d, J=8.7 Hz, 2H), 7.23 (d, J=8.7 Hz, 2H).

11β-[4-(N,N-dimethylamino)phenyl]-spiro-3α-oxiranyl-11β-hydroxy-5α-estrane

A 60% dispersion of NaH in mineral oil (0.16 g, 4.05 mmol) was added to a solution of trimethylsulfoxonium iodide (0.89 g, 4.05 mmol) in anhydrous DMSO (100 mL) under N$_2$. The solution was allowed to stir at room temperature for 2 h or until the evolution of gas ceased. A solution of 11β-[4-(N,N-dimethylamino)phenyl]-5α-17β-hydroxy-estr-3-one (0.80 g, 2.02 mmol) in anhydrous DMSO (15 mL) was then added in a dropwise manner. The suspension was allowed to stir at room temperature for 8 h and a saturated solution of NaCl (200 mL) was added. The biphasic mixture was extracted with CH$_2$Cl$_2$ (3×150 mL) and the organic extracts were combined, dried (MgSO$_4$) and concentrated under reduced pressure. The resulting oil was purified on silica using medium pressure column chromatography (petroleum ether/acetone, 8:2) to provide 11β-[4-(N,N-dimethylamino)phenyl]-spiro-3α-oxiranyl-17β-hydroxy-5α-estrane as a colorless oil (0.40 g, 48%). $^1$H-NMR (300 MHz, CDCl$_3$) δ 0.45 (s, 3H), 0.98-1.99 (m, 23H), 2.07 (d, J=13.2 Hz, 1H), 2.49 (d, J=4.8 Hz, 1H), 2.53 (d, J=4.8 Hz, 1H), 2.87 (s, 6H), 3.20 (m, 1H), 3.47 (dd, J=7.8, 7.8 Hz, 1H), 6.58 (d, J=8.7 Hz, 2H), 7.19 (d, J=8.7 Hz, 2H).

11β-[4-(N,N-dimethylamino)phenyl]-1-hydroxy-3β-methyl-17β-hydroxy-5α-estrane

A solution of 11β-[4-(N,N-dimethylamino)phenyl]-spiro-3α-oxiranyl-17β-hydroxy-5α-estrane (0.40 g, 0.98 mmol) in THF (15 mL) was added in a dropwise manner to a well stirred suspension of LiAlH$_4$ (0.11 g, 2.94 mmol) in anhydrous THF (50 mL) at 0° C. under N$_2$. The suspension was allowed to warm to room temperature and kept at room temperature for 8 h. Celite (1.0 g) was added followed by H$_2$O (0.15 mL) and 10% NaOH (0.15 mL). The viscous suspension was filtered through a sintered glass funnel and the filter cake was washed with $CH_2Cl_2$ (2×50 mL). The resulting filtrate was concentrated under reduced pressure to provide a white solid. The solid was taken up in MeOH (25 mL) and a 1.0 M solution of HCl in anhydrous ether (1.0 mL) was added. The solution was concentrated under reduced pressure and the resulting solid was recrystallized from $CH_3CN$/petroleum ether to provide 11β-[4-(N,N-dimethylamino)phenyl]-3α-hydroxy-β-methyl-17β-hydroxy-5α-estrane hydrochloride as a white solid (0.43 g, 94%). mp. 230-232° C. dec. $^1$H-NMR (300 MHz, $CD_3OD$) δ 0.19 (s, 3H), 0.85 (s, 3H), 0.62-1.80 (m, 24H), 1.90-1.95 (d, J=13.2 Hz, 1H), 3.05 (s, 6H), 3.17 (m, 1H), 3.27-3.32 (dd, J=8.7, 8.7 Hz, 1H), 7.23-7.26 (d, J=8.4 Hz, 2H), 7.43-7.46 (d, J=8.4 Hz, 21-1). Elemental Anal. for $C_{27}H_{42}ClNO_2 \cdot 0.25H_2O$ Calcd. C: 71.65, H: 9.46, N: 3.09 Found. C: 71.90, H: 9.46, N: 3.25.

11β-[4-(N,N-dimethylamino)phenyl]-3β-hydroxy-3β-methyl-5α-estra-17-one

Tetrapropylammonium perruthenate (0.35 g, 0.10 mmol) was added to a solution of 11β-[4-(N,N-dimethylamino)phenyl]-3α-hydroxy-β-methyl-17β-hydroxy-5α-estrane (0.38 g, 0.91 mmol), 4-methylmorpholine-N-oxide (0.21 g, 1.82 mmol), and 4 Å powdered molecular sieves (0.05 g) in anhydrous $CH_2Cl_2$ (50 mL) at room temperature under $N_2$. The black suspension was allowed to stir for 10 h and tetrapropylammonium perruthenate (0.21 g, 0.60 mmol) was again added. The black suspension was allowed to stir at room temperature for an additional 3 h and was filtered through a pad of Celite. The filtrate was concentrated under reduced pressure and the resulting black oil was purified on silica using medium pressure column chromatography (petroleum ether/acetone, 8.5:1.5) to provide 11β-[4-(N,N-dimethylamino)phenyl]-3α-hydroxy-β-methyl-5α-estra-17-one hydrochloride as a white solid (0.10 g, 28%). The hydrochloride salt was prepared through the addition of 1.1 eq. of 1.0 M HCl in anhydrous $Et_2O$ to the amine in EtOAc. The resulting solid was filtered, washed with $Et_2O$ and dried. mp. 222-225° C. dec. $^1$H-NMR (300 MHz, $CD_3OD$) 0.67 (s, 3H), 1.12 (s, 3H), 1.01-1.74 (m, 18H), 1.97 (m, 1H), 2.00-2.21 (m, 4H), 2.46-2.57 (m, 1H), 3.36 (s, 6H), 3.57 (m, 1H), 7.54-7.57 (d, J=8.4 Hz, 2H), 7.70-7.79 (d, J=8.4 Hz, 2H). Elemental Anal. for $C_{25}H_4ClNO_2 \cdot 0.25H_2O$ Calcd. C: 71.97, H: 9.05, N: 3.10 Found. C: 71.95, H: 9.09, N: 3.07.

11β-[4-(N,N-dimethylamino)phenyl]-3α-hydroxy-3β-methyl-5α-estrane-17-oxime

Hydroxylaminehydrochloride (0.038 g, 0.54 mmol) was added to a solution of 11β-[4-(N,N-dimethylamino)phenyl] 4-hydroxy-3β-methyl-R-estra-17-one (0.10 g, 0.24 mmol) in anhydrous pyridine (20 mL) at room temperature under $N_2$. The solution was allowed to stir at room temperature for 18 h and saturated $NaHCO_3$ (100 mL) was added. The biphasic mixture was extracted with $CH_2Cl_2$ (3×100 mL) and the organic extracts were combined, dried ($MgSO_4$), and concentrated under reduced pressure to provide 11β-[4-(N,N-dimethylamino)phenyl]-3α-hydroxy-3β-methyl-5α-estrane-17-oxime as a white solid (0.10 g, 98%). The product was used without further purification. $^1$H-NMR (300 MHz, $CD_3OD$) δ 0.55 (s, 3H), 0.98 (s, 3H), 0.98-1.36 (m, 18H), 1.76-1.88 (m, 4H), 2.09 (m, 1H), 2.32 (m, 2H), 2.77 (s, 6H), 3.20 (m, 1H), 6.58-6.61 (d, J=8.7 Hz, 2H), 7.15-7.18 (d, J=8.7 Hz, 2H).

11β-[4-(N,N-dimethyl-N-(oxy)amino)phenyl]-3α-hydroxy-3β-methyl-5α-estrane-17-oxime A solution of 11β-[4-(N,N-dimethylamino)phenyl]-3α-hydroxy-3α-methyl-5α-estrane-17-oxime (0.10 g, 0.24 mmol) in $CH_2Cl_2$ (5 mL) was added in a dropwise manner to a well stirred solution of hexafluoroacetone (0.026 g, 0.12 mmol) and 30% $H_2O_2$ (0.053 mL, 0.47 mmol) in $CH_2Cl_2$ (15 mL). The solution was allowed to stir vigorously at room temperature for 3 h and $H_2O$ (50 mL) was added. The biphasic mixture was extracted with $H_2O$ (3×50 mL) and the aqueous extracts were combined and concentrated under reduced pressure to provide 11β-[4-(N,N-dimethyl-N-(oxy)amino)phenyl]-3-hydroxy-3β-methyl-5α-estrane-17-oxime as a white solid (0.10 g, 99%). The solid was used without further purification. $^1$H-NMR (300 MHz, $CD_3OD$) δ 0.60 (s, 3H), 1.10 (s, 3H), 0.63-1.66 (m, 18H), 1.87-2.05 (m, 4H), 2.23-2.28 (d, J=13.5 Hz, 1H), 2.44 (m, 2H), 3.47 (m, 1H), 3.60 (s, 6H), 7.63-7.66 (d, J=8.7 Hz, 2H), 7.85-7.88 (d, J=8.7 Hz, 2H).

11β-[4-(N,N-dimethylamino)phenyl]-3α-hydroxy-3β-methyl-17β-nitro-5α-estrane $KHCO_3$ (0.20 g, 2.04 mmol) in $H_2O$ (2 mL) was added to a well stirred solution of NBS (0.18 g, 1.02 mmol) in dioxane (8 mL). The suspension was allowed to stir at room temperature for 0.25 h and a solution of 11β-[4-(N,N-dimethyl-N-(oxy)amino)phenyl]-3α-hydroxy-3β-methyl-5α-estrane-17-oxime (0.15 g, 0.34 mmol) in dioxane (2 mL) and $H_2O$ (2 mL) was added. The pale green solution was allowed to stir at room temperature for 10 h and a freshly prepared aqueous solution of saturated $FeSO_4$ (50 mL) was added. The brown suspension was allowed to vigorously stir at room temperature for 0.25 h and was extracted with EtOAc (3×100 mL). The organic extracts were combined, washed with saturated $FeSO_4$ (3×100 mL), dried ($MgSO_4$), and concentrated under reduced pressure. The resulting brown oil was taken up in THF/$H_2O$ (20:2, 22 mL) and cooled to 0° C. $NaBH_4$ (0.09 g, 2.38 mmol) was added and the solution was allowed to warm to room temperature and stir for 2 h. Water (50 mL) was added and the biphasic mixture was extracted with $CH_2Cl_2$ (3×100 mL). The organic extracts were combined, dried ($MgSO_4$) and concentrated under reduced pressure. The resulting oil was purified on silica using medium pressure column chromatography (petroleum ether/acetone, 9:1) to provide 11β-[4-(N,N-dimethylamino)phenyl]-3α-hydroxy-3β-methyl-5α-17β-nitro-estrane as a white solid (0.010 g, 7%). $^1$H-NMR (500 MHz, $CDCl_3$) δ 0.48 (s, 3H), 1.13 (s, 3H), 0.86-1.63 (m, 17H), 1.76-1.82 (m, 1H), 1.84-1.95 (m, 3H), 1.99-2.07 (m, 1H), 2.36-2.39 (d, J=7.8 Hz, 1H), 2.42-2.51 (m, 1H), 2.99 (s, 6H), 3.29 (m, 1H), 4.27 (dd, J=5.4, 5.4 Hz, 1H), 6.60-6.62 (d, J=5.1 Hz, 2H), 7.19-7.21 (d, J=5.1 Hz, 2H). $^{13}$C-NMR (500 MHz, $CDCl_3$) 13.83, 23.49, 24.34, 25.20, 31.42, 31.89, 31.92, 33.11, 37.63, 38.28, 38.52, 38.78, 40.64, 42.16, 46.02, 46.21, 47.04, 50.89, 54.73, 69.61, 95.37, 112.07, 130.26, 132.18, 148.16. HRMS: [M+H]$^+$ for $C_{27}H_{40}N_2O_3$ Calcd. 441.3117. Found 441.3116.

The biological activity of compounds detailed in this invention were evaluated using in vitro and in vivo tests.

Radioligand Binding Assays

Tissue preparation. Rat brain cerebral cortex homogenates and the binding assays were conducted essentially as described (Carter et al., 1997). Briefly, adult male Sprague-Dawley rats (Charles River Laboratories, Raleigh, N.C.) were killed by excess $CO_2$ asphyxiation, decapitated, and their brain rapidly removed and frozen on dry ice before being stored −76° C. The frozen cortices were placed in 10 volumes of an ice-cold 0.32 M sucrose solution and homogenized with a Teflon-glass homogenizer. The homogenate was centrifuged at 1500×g (10 min at 4° C.). The supernatant was retained and centrifuged at 10,000×g (20 min at 4° C.), yielding the P2 pellet. The P2 pellet was resuspended in an equal volume of a 50 mM Na+/K+ phosphate buffer containing 200 mM NaCl (pH 7.4) and centrifuged at 10,000×g (10 min at 4° C.). The pellet was washed twice more, resuspended in 1/10 volume of buffer and stored at −76° C. until the time of assay.

[$^{35}$S]TBPS binding assays. These assays were carried out in 1.4 mL polypropylene tubes (Matrix Technologies, Hudson, N.H.). In a final volume of 0.5 mL, each tube contained 100 μL, cortical membrane suspension (40 μg of protein, added last) 2 nM [$^{35}$S]TBPS (64-165 Ci/mmol), 6.25 μM GABA and one of six different concentrations of test compound added as 5 μL in 100% DMSO (1% final DMSO concentration). The test compounds were added to the assay tubes using a BiomekFX automated liquid handler with 96-well head (Beckman-Coulter, Fullerton, Calif.). Nonspecific binding was determined in the presence of 200 μM picrotoxin. The assays were incubated for 2 h at RT before being terminated by vacuum filtration through 96-well GF/B glass filter plates using a 96-well harvester (Brandel Scientific, Gaithersburg, Md.). Prior to harvesting, the filter plates were pre-soaked for 20 min in buffer containing 0.15% BSA and 0.1% PEI. The radioactivity remaining on the filter was determined in a TopCount 12-detector scintillation counter (Packard Instruments, Meriden, Conn.) using 20 μl of MicroScint20 (Packard Instruments) per well and standard liquid scintillation counting techniques.

[$^{3}$H]Flunitrazepam binding assay. This assay was conducted as described for the [$^{35}$S]TBPS assay except that the assays contained 20 μg tissue homogenate, 1.0 μM GABA and 1.0 nM [$^{3}$H]flunitrazepam (74.1-85 Ci/mmol). Clonazepam (1.0 μM) was used to determine nonspecific binding.

Data analysis. The $IC_{50}$ or $EC_{50}$ and $E_{max}$ values for allopregnanolone and the test compounds were calculated from a three-parameter logistic equation fit to the binding data using Prism (version 3, GraphPad Software, San Diego, Calif.) and are reported in Table 2 below.

TABLE 2

Lead Structures: Highly Potent and Efficacious Neuroactive Steroids

| Compound | Compound | [$^{3}$H]Flunitrazepam | | [$^{35}$S]TBPS |
| --- | --- | --- | --- | --- |
| | | $EC_{50}$ (nM) | $E_{max}$ (%) | $IC_{50}$ (nM) |
| Allopregnanolone | A2-A | 26 ± 9.9 | 100% | 12.6 ± 1.7 |
| A2-A | A2-B | 24 ± 2.5 | 103% | 13 ± 0.13 |
| A2-B | B-5 | 33.5 ± 4.9 | 99.1% | 17.9 ± 6.19 |
| B-5 | | 75.9 ± 12.4 | 131.7% | 32 ± 5.19 |

TABLE 2-continued

Lead Structures: Highly Potent and Efficacious Neuroactive Steroids

| Compound | Compound | [$^3$H]Flunitrazepam EC$_{50}$ (nM) | E$_{max}$ (%) | [$^{35}$S]TBPS IC$_{50}$ (nM) |
|---|---|---|---|---|
| C-8 | (structure) | 39.5 ± 20.6 | 135% | 9.79 ± 1.93 |

The E$_{max}$ values are for pregnanolone and the test compounds are presented as the percentage of E$_{max}$ determined for allopregnanolone. The average enhancement of [$^3$H]flunitrazepam measured in the presence of allopregnanolone was approximately 60%. In cases where limited inhibition of [$^{35}$S]TBPS or enhancement of [$^3$H]flunitrazepam occurred at the top concentration of 10,000 nM, the IC$_{50}$ or EC$_{50}$ values are given as >10,000 nM. The data for the active compounds are reported as the mean±SD from at least three independent experiments.

Testing in Mouse Models

Male NIH Swiss mice (25-30 g) were housed two per cage Animals were kept in a vivarium (temperature 22-26° C.; humidity 40-50%) with an artificial 12-h light/dark cycle and free access to food and water. Animals were allowed to acclimate to the vivarium for at least 5 days. The experiments were performed during the light phase of the light/dark cycle (between 9:30 AM and 3:30 PM), after at least a 30-min period of acclimation to the experimental room. Animals were maintained in facilities fully accredited by the Association for Assessment and Accreditation of Laboratory Animal Care, and experiments were performed under protocols approved by the Animal Care and Use Committee of the National Institute of Neurological Disorders and Stroke in strict compliance with the Guide for the Care and Use of Laboratory Animals of the National Research Council (National Academy Press, Washington, D.C.

Solutions of the steroids were made fresh daily in 40% hydroxypropyl-β-cyclodextrin in sterile 0.9% saline. Further dilutions were made using sterile saline. The steroids were injected intraperitoneally. The convulsant agent pentylenetetrazol (PTZ; Sigma-Aldrich) was dissolved in saline immediately before use. All drug solutions were administered in a volume equaling 0.01 mL/g of the animal's body weight.

The PTZ seizure test was carried out as described (Kokate et al., 1994). In brief, mice were injected subcutaneously with PTZ (80 mg/kg) 15 min after injection of the test steroid and were observed for a 30-min period. Mice failing to show clonic seizures lasting longer than 5 s were scored as protected. To construct dose-response curves, steroids were tested at several doses spanning the dose producing 50% protection (ED$_{50}$). Six to eight mice were tested at each dose. ED$_{50}$ values and corresponding 95% confidence limit were determined by log-probit analysis.

The 6-Hz seizure test was carried out 15 min after injection of the test steroid as described (Kaminski et al., 2004). In brief, 3-s corneal stimulation (200 μs-duration, 32-mA monopolar rectangular pulses at 6 Hz) was delivered by a constant current device (ECT Unit 5780; Ugo Basile, Comerio, Italy). Ocular anesthetic (0.5% tetracaine) was applied to the corneas 15 min before stimulation. In response to stimulation, the animals exhibited a "stunned" posture associated with rearing and automatic movements that lasted from 60-120 s in untreated animals. Animals resumed their normal exploratory behavior after the seizure. The experimental endpoint was protection against the seizure. An animal was considered to be protected if it resumed its normal exploratory behavior within 10 s of stimulation. The statistical comparisons were the same as described for the PTZ test.

Anxiolytic activity was assessed with the elevated zero-maze as described (Kaminski et al., 2006). The maze (Hamilton-Kinder, Poway, Calif.) was positioned in the center of a room under dim lighting. Each mouse was individually removed from its home cage and placed just inside a closed arm. Five-min test sessions were video-recorded with a tripod-mounted camcorder. Percent time in open areas and number of entries into open areas were scored from the taped records using Observer 3.0 software (Noldus, Wageningen, The Netherlands). An animal was considered to have entered an open area if all four paws had left the closed areas. Open-area time was considered terminated once a single paw was placed back into the closed area. Increases in these measures reflect anxiolytic activity. Dose-response data were analyzed by one-way analysis of variance. Differences from control (vehicle-treatment) values for individual doses were identified by post-hoc comparisons using the Dunnett's test.

The series of GABA$_A$ receptor ligands described herein display binding characteristics on par with the endogenous neurosteroid allopregnanolone.

It will now be apparent to those skilled in the art that numerous modifications and variations of the present invention are possible in light of the above teachings. It is therefore to be understood that, within the scope of the appended claims, the invention may be practiced otherwise than as specifically described herein without departing from the spirit and the scope of the present invention.

REFERENCES

U.S. Patent Documents

1. Upasani, R. B.; Xia, H. Methods, Compositions and Compounds for Allosteric Modulation of the GABA Receptor by Members of the Androstane and Pregnane Series, U.S. Pat. No. 6,143,736, Nov. 7, 2000.
2. Upasani, R. B.; Xia, H. Method, Compositions, and Compounds for Allosteric Modulation of the GABA Receptor by Members of the Androstane and Pregnane Series, U.S. Pat. No. 5,939,545, Aug. 17, 1999.
3. Upasani, R. B.; Fick, D. B.; Hogenkamp, D. J.; Lan, N. C. Neuroactive Steriod of the Androstane and Prgnane Series, U.S. Pat. No. 5,925,630, Jul. 20, 1999.
4. Upasani, R. B.; Xia, H.; Hogenkamp, D. J. Methods for Allosteric Modulation of the GABA Receptor by Members of the Androstane and Pregnane Series, U.S. Pat. No. 6,277,838 B1, Aug. 21, 2001.
5. Patchett, A. A.; Metuchen, G. E.; Arth, C.; Hoffman, F. G. Alkanoylthio and Pyrazolo Androstane Derivatives, U.S. Pat. No. 3,094,521, Jun. 18, 1963.

Other Publications

1. Belelli, D., Lambert, J. J., 2005. Neurosteroids: endogenous regulators of the $GABA_A$ receptor. *Nat. Rev. Neurosci.* 6, 565-575.
2. Carter, R. B., Wood, P. L., Wieland, S., Hawkinson, J. E., Belelli, D., Lambert, J. J., White, H. S., Wolf, H. H., Mirsadeghi, S., Tahir, S. H., Bolger, M. B., Lan, N. C., Gee, K. W., 1997. Characterization of the anticonvulsant properties of ganaxolone (CCD 1042; 3α-hydroxy-3β-methyl-5α-pregnan-20-one) a selective, high-affinity, steroid modulator of the $\gamma$-aminobutyric $acid_A$ receptor. *J. Pharmacol. Exp. Ther.* 280, 1284-1295.
3. Gasior, M., Carter, R. B., Witkin, J. M., 1999. Neuroactive steroids: potential therapeutic use in neurological and psychiatric disorders. *Trends Pharmacol. Sci.* 20, 107-112.
4. Hogenkamp, D. J., Tahir, S. H., Hawkinson, J. E., Upasani, R. B., Alauddin, M., Kimbrough, C. L., Acosta-Burruel, M., Whittemore, E. R., Woodward, R. M., Lan, N.C., Gee, K. W., Bolger, M. B., 1997. Synthesis and in vitro activity of 3β-substituted-3α-hydroxypregnan-20-ones:allosteric modulators of the $GABA_A$ receptor. *J. Med. Chem.* 40, 61-72.
5. Kaminski, R. M., Livingood, M. R., Rogawski, M. A., 1994. Allopregnanolone analogs that positively modulate GABA receptors protect against partial seizures induced by 6-Hz electrical stimulation in mice. *Epilepsia* 45, 864-867.
6. Kaminski, R. M., Marini, H., Ortinski, P. I., Vicini, S., Rogawski, M. A., 2006. The pheromone androstenol (5α-androst-16-en-3α-ol) is a neurosteroid positive modulator of $GABA_A$ receptors. *J. Pharmacol. Exp. Ther.* 317:694-703.
7. Kokate, T. G., Svensson, B. E., Rogawski, M. A., 1994. Anticonvulsant activity of neurosteroids: correlation with γ-aminobutyric acid-evoked chloride current potentiation. *J. Pharmacol. Exp. Ther.* 270, 1223-1229.
8. Monaghan, E. P., McAuley, J. W., Data, J. L., 1999. Ganaxolone: a novel positive allosteric modulator of the $GABA_A$ receptor complex for the treatment of epilepsy. *Expert Opin. Investig. Drugs* 8, 1663-1671.
9. Rogawski, M. A., 2006. Diverse mechanisms of antiepileptic drugs in the development pipeline. *Epilepsy Res.* 69, 273-294.
10. Rupprecht, R., 2003. Neuroactive steroids: mechanisms of action and neuropsychopharmacological properties. *Psychoneuroendocrinology* 28, 139-168.
11. Wittmer, L. L., Hu, Y., Kalkbrenner, M., Evers, A. S., Zorumski, C. F., Covey, D. F., 1996. Enantioselectivity of steroid-induced $\gamma$-aminobutyric $acid_A$ receptor modulation and anesthesia. *Mol. Pharmacol.* 50, 1581-1586
12. Patchett, A. A.; Hoffman, F. G.; Giarrusso, F. F.; Schwam, H.; Arth, G. E. The Synthesis of 17β-Amino-17α(2'-carboxyethyl)androstane Lactams. *J. Org. Chem.* 1962, 27, 3822.
13. Hamilton N M (2002) Interaction of steroids with the GABA(A) receptor. *Curr. Top Med Chem* 2:887-902.
14. Wang M D, He Y J, Eisenman L N, Fields C, Zeng C M, Mathews J, Benz A, Fu T, Zorumski E, Steinbach J H, Covey D F, Zorumski C F, and Mennerick S (2002) 3 Beta-Hydroxypregnane Steroids Are Pregnenolone Sulfate-Like Gaba(a) Receptor Antagonists. *J. Neuroscience* 22:3366-3375.

What is claimed is:

1. A compound of structure 3, wherein:

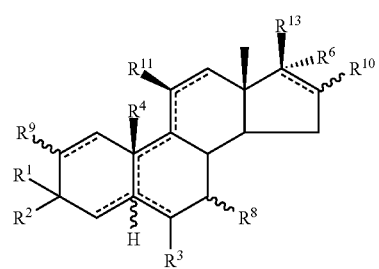

$R^1$ is H or (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle, 2-heterocycle-substituted ethynyl, heterocycle-substituted $C_{1-4}$ alkyl, heterocycle-substituted $C_{2-4}$-alkenyl, or heterocycle-substituted $C_{3-6}$ cycloalkyl;

$R^2$ group is OH or $OR^{14}$, where $R^{14}$ is HCO— or (optionally substituted) $C_{1-18}$ alkyl-CO— (except that $R^{14}$ is not $CH_3$ when $R^1$, $R^2$, $R^3$, $R^6$, $R^8$, $R^9$ and $R^{10}$=H, $R^4$=$CH_3$, and there are no double bonds present), $C_{2-18}$ alkenyl-CO—, $C_{2-18}$ alkynyl-CO—, $C_{6-10}$ aryl-CO— or heterocycle-CO—; or $R^{14}$ is (optionally substituted) $C_{1-18}$ alkyl-X—CO—, $C_{2-18}$ alkenyl-X—CO—, $C_{2-18}$ alkynyl-X—CO—, $C_{6-10}$ aryl-X—CO— or heterocycle-X—CO—; or $R^{14}$ is trimethylsilyl or triethylsilyl; or $R^{14}$ is (optionally substituted) $C_{1-4}$ alkyl, $C_{3-6}$ cycloalkyl, $C_{2-4}$ alkenyl, or $C_{2-4}$ alkynyl, or; or $R^{14}$ is HO—$SO_2$— or a salt thereof or $R^2$ is $NR^{15}R^{16}$, where $R^{15}$ is H, OH or (optionally substituted) $C_{1-4}$ alkyl, $C_{3-6}$ cycloalkyl, $C_{2-4}$ alkynyl, $C_{2-4}$ alkenyl, $C_{6-10}$ aryl, heterocycle or $R^{15}$ is $OR^{17}$, where $R^{17}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, $C_{1-18}$ alkyl-CO—, $C_{2-18}$ alkenyl-CO—, $C_{2-18}$ alkynyl-CO—, $C_{6-10}$ aryl-CO— or heterocycle-CO—; and where $R^{16}$ is H or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle, or $R^{16}$ is H—CO— or (optionally substituted) $C_{1-18}$ alkyl-CO—, $C_{2-18}$ alkenyl-CO—, $C_{2-18}$ alkynyl-CO—, $C_{3-6}$ cycloalkyl-CO—, $C_{6-10}$ aryl-CO— or heterocycle-CO—;

where X is O or $NR^{100}$, where $R^{100}$ is (optionally substituted) $C_{1-4}$ alkyl, $C_{3-6}$ cycloalkyl, $C_{2-4}$ alkenyl, $C_{2-4}$ alkynyl $C_{6-10}$ aryl or heterocycle; or X is $NOR^{110}$, where $R^{110}$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which is optionally substituted; or X is

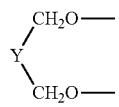

where Y is —$(CH_2)_m$— where m is an integer of 0 to 3, or Y is —$(CH_2)_n$—Z—$(CH_2)_p$— where n is an integer of 0 to 2, p is an integer of 0 to 2 and Z is a heteroatom (optionally substituted) or Z is a carbon atom substituted with one or two $C_{1-6}$ alkyl groups;

$R^3$ is H, halogen, cyano, azido or (optionally substituted) $C_{1-4}$ alkyl, $C_{3-6}$ cycloalkyl, $C_{2-4}$ alkynyl, $C_{2-4}$ alkenyl, $C_{6-10}$ aryl, or heterocycle;

$R^4$ is H or (optionally substituted) Me;

$R^6$ is H, or (optionally substituted) $C_{1-8}$ alkyl, $C_{3-6}$ cycloalkyl, $C_{2-8}$ alkenyl, $C_{2-8}$ alkynyl, $C_{6-10}$ aryl or heterocycle;

$R^8$ is H, halogen, azido, cyano, thiocyano, =O, OH, $OR^{16}$ (where $R^{16}$ is as defined above); or $R^8$ is $NH_2$ or $NR^{15}R^{16}$ (where $R^{15}$ and $R^{16}$ are as defined above); or $R^8$ is (optionally substituted) $C_{1-18}$ alkyl, $C_{3-6}$ cycloalkyl, $C_{2-18}$ alkynyl, $C_{2-18}$ alkenyl, $C_{6-10}$ aryl or heterocycle; or $R^8$ is $COOR^{18}$ where $R^{18}$ is (optionally substituted) $C_{1-4}$ alkyl, $C_{3-6}$ cycloalkyl, $C_{2-4}$ alkenyl, $C_{2-4}$ alkynyl, $C_{6-10}$ aryl, or heterocycle; or $R^8$ is $S(O)_nR^{16}$, where $R^{16}$ is as defined above and n=0, 1, or 2;

$R^9$ is H, cyano, azido, halogen, thiocyano, OH, $OR^{16}$, where $R^{16}$ is as described above, or $R^9$ is (optionally substituted) $C_{1-4}$ alkyl, $C_{3-6}$ cycloalkyl, $C_{2-4}$ alkynyl, $C_{2-4}$ alkenyl, $C_{6-10}$ aryl, 2-arylsubstituted ethynyl, arylsubstituted $C_{1-4}$ alkyl, arylsubstituted $C_{2-4}$-alkenyl, arylsubstituted $C_{3-6}$ cycloalkyl, heterocycle; 2-heterocycle-substituted ethynyl, heterocycle-substituted $C_{1-4}$ alkyl, heterocycle-substituted $C_{2-4}$-alkenyl, heterocycle-substituted $C_{3-6}$ cycloalkyl;

$R^{10}$ is H, keto, halogen, cyano, thiocyano, azido or $NR^{15}R^{16}$, where $R^{15}$ and $R^{16}$ are as described above in the definition of $R^2$; or $R^{10}$ is (optionally substituted) $C_{1-4}$ alkyl, $C_{3-6}$ cycloalkyl, $C_{2-4}$ alkynyl, $C_{2-4}$ alkenyl, $C_{6-10}$ aryl or heterocycle; or $R^{10}$ is $OR^{16}$;

where $R^{16}$ is as described above in the definition of $R^2$; or $R^{16}$ is trimethylsilyl or triethylsilyl; or $R^{16}$ is =$CH_2$ or =$CHR^{19}$, where $R^{19}$ is (optionally substituted) $C_{1-4}$ alkyl, $C_{3-6}$ cycloalkyl, $C_{2-4}$ alkynyl, $C_{2-4}$ alkenyl or $C_{6-10}$ aryl; or $R^{10}$ is $S(O)_nR^{16}$, where $R^{16}$ is as defined above in the definitions of $R^2$ and $R^{10}$; and n=0, 1, or 2;

$R^{11}$ is $C_{1-18}$ alkyl, $C_{2-18}$ alkenyl, $C_{2-18}$ alkynyl, $C_{3-8}$ cycloalkyl, $C_{6-12}$ aryl, aralkyl, aralkenyl, aralkynyl, heteroaryl, heteroaralkyl, heteroaralkenyl or heteroaralkynyl any of which is optionally substituted;

or $R^{11}$ is

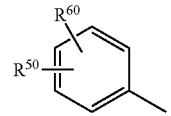

where $R^{50}$ and $R^{60}$ are each independently H; halogen; $(R^{70}R^{80}N(O)_r)$—, where r is 0 or 1 and $R^{70}$ and $R^{80}$ are each independently H, $C_{1-6}$ alkyl, $C_{3-8}$ cycloalkyl, $C_{2-6}$ alkenyl or $C_{2-6}$ alkynyl, any of which is optionally substituted; substructure II,

II

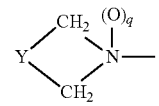

where q is 0 or 1, Y is —$(CH_2)_m$— where m is an integer of 0 to 5, or Y is $(CH_2)_n$—Z—$(CH_2)_p$— where n is an integer of 0 to 2, p is an integer of 0 to 2, and Z is a heteroatom (optionally substituted) and where the $CH_2$ groups are optionally substituted; N-imidazolyl; —N-pyrrolyl-; HO—; $CF_3SO_2O$—; $C_{1-6}$ alkyl-O—; $C_{1-6}$ perfluoroalkyl-O—; $C_{1-6}$ alkyl-S—; $C_{1-6}$ alkyl-CH(OH)—; NC—; HCC—; $C_6H_5CC$—; 2'-furyl; 3'-furyl; 2'-thiophenyl; 3'-thiophenyl; 2'-pyridyl; 3'-pyridyl; 4'-pyridyl; 2'-thiazolyl; 2'-N-methylimidazolyl; 5'-pyrimidinyl; $C_6H_5$—; $H_2C$=CH—; $C_{1-6}$ alkyl; MeC(=$CH_2$)—; $C_{1-6}$ alkyl-CO; HCO; $C_{1-6}$ alkyl; C=$NOR^{120}$, or HC=$NOR^{120}$, where $R^{120}$ is H or $C_{1-6}$ alkyl, $C_{3-8}$ cycloalkyl, $C_{2-6}$ alkenyl, $C_{2-6}$ alkynyl, $C_{6-12}$ aryl, or heteroaryl, any of which is optionally substituted; or $R^{50}$ and $R^{60}$ combine to form a ring

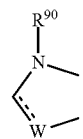

where W is $CH_2$, CH, NH, N, O, or S, and $R^{90}$ is H or $C_{1-6}$ alkyl; or $R^{50}$ and $R^{60}$ combine to form a ring

where A and B are each independently H, F or $C_{1-6}$ alkyl or A and B combine to form =O; or $R^{50}$ and $R^{60}$ combine to form a ring

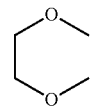

where the $CH_2$ groups are independently and optionally substituted; and $R^{13}$ is one of hydrogen, thio-$C_{1-4}$-alkyl, thio-$C_{2-4}$-alkenyl, cyano, aminocarbonyl, mono-$C_{1-4}$-alkylaminocarbonyl, di-$C_{1-4}$-alkylaminocarbonyl, sulfinyl, sulfonyl, thio, sulfonamido, $C_{2-4}$-alkynyloxy, optionally substituted $C_{6-10}$ aryloxy, optionally substituted $C_{6-10}$ aryl-$C_{1-4}$-alkyloxy, an optionally substituted 1,3-dioxolan-4-one of an acetyl group, an optionally substituted 1,3-dioxan-4-one of an acetyl group, an optionally substituted 1,3-oxathiolan-5-one of an acetyl group, an optionally substituted 1,3-oxathioan-5-one of an acetyl group, —O—C(O)—NR'R", —C(O)—CH$_2$-J-G, —C(O)—CH$_2$-O-T, —C(O)—CH$_2$-O-E, —C(O)—CH$_2$-Q-G, —C(O)—CH$_2$-J'-Q-G, or —C(O)—CH$_2$-J'-Q-L, wherein R' and R" independently represent hydrogen or optionally substituted $C_{1-4}$ alkyl, or taken together with the nitrogen to which they are attached form a 3- to 6-membered heterocyclic ring;

J is one of S, SO or $SO_2$;

J' is one of O, S, SO or $SO_2$;

Q is one of $C_{1-4}$ alkyl, $C_{2-4}$ alkenyl or $C_{2-4}$ alkynyl;

G is one of C-attached hetero-$C_{5-10}$-aryl, optionally substituted $C_{6-10}$ aryl, a quaternary ammonium salt of a nitrogen containing hetero-$C_{5-10}$-aryl group or a quaternary salt of an amino substituted $C_{6-10}$ aryl group;

T is C-attached hetero-$C_{5-10}$-aryl or a quaternary ammonium salt of a nitrogen containing hetero-$C_{5-10}$-aryl group;

E is optionally substituted $C_{6-10}$ aryl or a quaternary ammonium salt of an amino substituted $C_{6-10}$ aryl group;

L is one of amino, amido, cyano, thiocyano, azido, nitro, hydroxy, halo, carboxyl, $C_{1-4}$ alkoxy, $C_{1-4}$ alkoxycarbonyl, $C_{1-4}$ alkanoyloxy, hydrogen, sulfate, thiosulfate, sulfonate, $C_{1-4}$ alkylthio, $C_{1-4}$ alkylsulfinyl, $C_{1-4}$ alkylsulfonyl or mercapto;

and stereoisomers and pharmaceutically acceptable salts thereof.

2. A pharmaceutical composition, comprising:
the compound according to claim 1, and
a pharmaceutically acceptable carrier.

3. A method for treatment of a condition responsive to GABA receptor modulating activity selected from the group consisting of convulsions, epilepsy, depression, drug and alcohol abuse, and anxiety in humans or animals, comprising:
administering, to a human or animal in need thereof, a pharmaceutical composition comprising an effective GABA receptor modulating amount of the compound of claim 1 and a pharmaceutically acceptable carrier.

* * * * *

UNITED STATES PATENT AND TRADEMARK OFFICE
CERTIFICATE OF CORRECTION

PATENT NO. : 10,087,211 B2
APPLICATION NO. : 15/341573
DATED : October 2, 2018
INVENTOR(S) : Scott P. Runyon et al.

It is certified that error appears in the above-identified patent and that said Letters Patent is hereby corrected as shown below:

On the Title Page

On page 2, Column 2, item (56), Line 9, "3βOL" should read --3β-OL--

On page 2, Column 2, item (56), Line 25, "Antaganists" should read --Antagonists--

In the Drawings

In sheet 4 of 5, FIG 4, "A-1b." should read --A-1b--

In the Specification

Column 1, Line 49, "ganaxalone" should read --ganaxolone--

Column 1, Line 66, "substitutent" should read --substituent--

Column 3, Line 55, "FBPS" should read --TBPS--

Column 3, Lines 56, "Novel structural features" should start as a new paragraph on Line 57

Column 6, Line 27, "C6-10aryl" should read --C6-10 aryl--

Column 6, Line 58, "S(O)R16" should read --S(O)nR16--

Column 6, Line 67, "R8" should read --R5--

Column 10, Line 1, "C6-10" should read --C5-10--

Column 10, Line 25, "17β-[1" should read --17β-[(1--

Signed and Sealed this
Fourteenth Day of January, 2020

Andrei Iancu
*Director of the United States Patent and Trademark Office*

CERTIFICATE OF CORRECTION (continued)
U.S. Pat. No. 10,087,211 B2

Column 12, Line 57, "sheepgoats," should read --sheep, goats,--

Column 13, Line 14, "N-bromosuccinimidein" should read --N-bromosuccinimide in--

Column 15, Line 32, "3-" should read --3α--

Column 17, Line 25, "diatereomers" should read --diastereomers--

Column 17, Lines 53-54, "diatereomeric" should read --diastereomeric--

Column 17, Lines 62-63, "recrystallied" should read --recrystallized--

Column 18, Line 32, "11β-" should read --17β- --

Column 18, Line 56, "-1-", should read --3α--

Column 19, Line 18, "-3β-" should read -- -3α- --

Column 25, Line 14, "Steriod" should read --Steroid--

Column 25, Line 14, "Prgnane" should read --Pregnane--

Column 25, Line 65, "anovel" should read --a novel--

In the Claims

Column 26, Line 57, "alkynyl, or" should read --alkynyl;--